(12) United States Patent
Lynch et al.

(10) Patent No.: US 7,964,649 B2
(45) Date of Patent: Jun. 21, 2011

(54) HYDRINDANE ANALOGS HAVING SPHINGOSINE 1-PHOSPHATE RECEPTOR AGONIST ACTIVITY

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/470,011

(22) Filed: May 21, 2009

(65) Prior Publication Data

US 2009/0253760 A1    Oct. 8, 2009

Related U.S. Application Data

(63) Continuation of application No. PCT/US2007/085401, filed on Nov. 21, 2007.

(60) Provisional application No. 60/860,697, filed on Nov. 21, 2006, provisional application No. 60/956,378, filed on Aug. 16, 2007.

(51) Int. Cl.
*A61K 31/135* (2006.01)
*C07C 215/00* (2006.01)

(52) U.S. Cl. .......................................... 514/653; 564/355

(58) Field of Classification Search ............. 514/364, 514/653; 548/143, 131; 564/355
See application file for complete search history.

(56) References Cited

U.S. PATENT DOCUMENTS

| | | | |
|---|---|---|---|
| 3,153,092 | A | 10/1964 | Burger |
| 4,939,130 | A | 7/1990 | Jaeggi et al. |
| 5,405,988 | A | 4/1995 | Klar et al. |
| 6,069,251 | A | 5/2000 | Thurkauf et al. |
| 6,875,757 | B2 | 4/2005 | Miller et al. |
| 7,060,697 | B2 | 6/2006 | Marsilje et al. |
| 7,064,217 | B2 | 6/2006 | Macdonald et al. |
| 7,241,790 | B2 | 7/2007 | Lynch et al. |
| 7,638,637 | B2 | 12/2009 | Lynch et al. |
| 2004/0224941 | A1 | 11/2004 | Seko et al. |
| 2005/0023386 | A1 | 2/2005 | Nishi et al. |
| 2005/0032744 | A1 | 2/2005 | Michaelis et al. |
| 2005/0107447 | A1 | 5/2005 | Lynch et al. |
| 2006/0046979 | A1 | 3/2006 | Foster et al. |
| 2006/0122181 | A1 | 6/2006 | Ikemoto et al. |
| 2006/0135786 | A1 | 6/2006 | Saha et al. |
| 2006/0211656 | A1 | 9/2006 | Albert et al. |
| 2006/0223866 | A1 | 10/2006 | Evindar et al. |
| 2007/0191313 | A1 | 8/2007 | Beard et al. |
| 2008/0249070 | A1 | 10/2008 | Lynch et al. |
| 2009/0042955 | A1 | 2/2009 | Lynch et al. |
| 2009/0062238 | A1 | 3/2009 | Lynch et al. |
| 2009/0105315 | A1 | 4/2009 | Lynch et al. |
| 2009/0137531 | A1 | 5/2009 | Lynch et al. |
| 2009/0253759 | A1 | 10/2009 | Lynch et al. |
| 2009/0253761 | A1 | 10/2009 | Lynch et al. |

FOREIGN PATENT DOCUMENTS

| | | |
|---|---|---|
| DE | 1 056 139 | 4/1959 |
| DE | 3 544 373 A1 | 6/1987 |
| EP | 1 553 091 A1 | 7/2005 |
| EP | 1 602 660 A1 | 12/2005 |
| GB | 950388 | 2/1964 |
| JP | 1994 135935 | 5/1994 |
| JP | 1994 135936 | 5/1994 |
| JP | 2002 316985 | 10/2002 |
| JP | 2004 307442 | 4/2004 |
| WO | WO 99/35259 | 7/1999 |
| WO | WO 01/60819 A1 | 8/2001 |
| WO | WO 01/71022 A2 | 9/2001 |
| WO | WO 02/076995 A2 | 10/2002 |
| WO | WO 02/092068 A1 | 11/2002 |
| WO | WO 03/059880 A1 | 7/2003 |
| WO | WO 03/061567 A2 | 7/2003 |
| WO | WO 2004/010987 A2 | 2/2004 |
| WO | WO 2004/017917 A2 | 3/2004 |
| WO | WO 2004/024673 A1 | 3/2004 |
| WO | WO 2004/028521 A2 | 4/2004 |
| WO | WO 2004/031129 A2 * | 4/2004 |
| WO | WO 2004/047743 A2 | 6/2004 |
| WO | WO 2004/096752 A1 | 11/2004 |
| WO | WO 2004/096757 A1 | 11/2004 |
| WO | WO 2004/103279 A2 | 12/2004 |
| WO | WO 2004/103306 A2 | 12/2004 |
| WO | WO 2005/032465 A2 | 4/2005 |
| WO | WO 2005/118523 A1 | 12/2005 |
| WO | WO 2006/001463 A1 | 1/2006 |
| WO | WO 2006/020951 A1 | 2/2006 |
| WO | WO 2007/085451 A2 | 8/2007 |
| WO | WO 2007/086001 A2 | 8/2007 |
| WO | WO 2007/091396 A1 | 8/2007 |
| WO | WO-2008064320 A2 | 5/2008 |
| WO | WO-2008064320 A3 | 5/2008 |
| WO | WO 2008-079382 | 7/2008 |
| WO | WO 2009/023854 A1 | 2/2009 |
| WO | WO 2009/043013 A2 | 4/2009 |
| WO | WO 2009/146112 A2 | 12/2009 |

OTHER PUBLICATIONS

Koo et al., Synthesis in the 5-Hydroxyindole Series. N-Acetyl-5-hydroxytryptophan and Related Compounds, 1959, Journal of Organic Chemistry, 24, 179-83.* Clemens, J J, "Synthesis of benzimidazole based analogues of sphingosine-1-phosphate: discovery of potent, subtype-selective S1P4 receptor agonists", Bioorganic & Medicinal Chemistry Letters, Oxford, GB vol. 14, No. 19, ISSN: 0960-894x, (Oct. 4, 2004), 4903-4905.
International Search Report for PCT/US2007/085401 Apr. 30, 2008.
Bandini, M. et al., *Eur. J. Chem.* 2001, 1937-1942.
Beilstein, Registry No. 6240345, 1985.
Bertus, P. et al., *Chem Commun*, 2001, 1792-1793.
Brinkmann, V. et al., *Transplantation* 72, 2001, 764-769.
Brinkmann, V. et al., *J Biol Chem* 277, 2002, 21453-21457.
Burger, A. et al., *Journal of Medicine and Pharmaceutical Chemistry*, vol. 4, No. 3, 1961.
Chiba, K. et al., *J Immunol* 160, 1998, 5037-5044.
Choi, D. et al., *J Med Chem* 39, 1996, 1907-1916.
Clair, T. et al., *Cancer Res* 63, 2003, 5446-5453.
Clemens, J. et al., *Bioorg Med Chem Lett* (2003), 3401-3404.

*Primary Examiner* — Kamal A Saeed
*Assistant Examiner* — Kristin Bianchi
(74) *Attorney, Agent, or Firm* — Schwegman, Lundberg & Woessner, P.A.

(57) ABSTRACT

Hydrindane analogs that have agonist activity at one or more of the S1P receptors are provided. The compounds are sphingosine analogs, which, after phosphorylation, can behave as agonists at S1P receptors.

19 Claims, 11 Drawing Sheets

OTHER PUBLICATIONS

Clemens, J. et al., *Bioorg. & Med. Chem. Lett.* (2004), 4903-4906.
Clemens, J. et al., *Bioorg. & Med. Chem. Lett.* (2005), 2005, 3568-3572.
Crosignani, S. et al., *Tetrahedron* 54, (1998), 15721-15730.
Davis, M. et al., *The J. of Bio. Chem.*, (2005), 9833-9841.
Dworkin, R. H. et al., *Arch. Neurol.*, 60, 2003, p. 1524-1534.
Forrest, M. et al., *J Pharmacol Exp Ther* 309, 2004, 758-768.
Foss, F. et al., *Bioorganic & Medicinal Chemistry* 15, 2005, 4470-4874.
Foss, F. et al., *Bioorganic & Medicinal Chemistry* 15, 2007, 663-677.
Fujino, M. et al., *J Pharmacol Exp Ther* 305, 2003, 70-77.
Graler, M. H. et al., *FASEB* 18, 2004, 551-553.
Hale, Jeffrey J. et al., *Bioorganic & Medicinal Chemistry Letters* 14, 2004, 3351-3355.
Hale, J. J. et al., 2004 *Bioorg Med Chem Lett* 14, 2004, 3501-3505.
Hale, J. J. et al., (2004) *Bioorg Med Chem Lett* 14, 3495-3499.
Hale, J. J. et al., *J Med Chem*, 2004, 47, 6662-6665.
Hanessian, S. et al., *Bioorganic & Medicinal Chemistry Letters* 17, 2007, 491-494.
Hoshino, Y. et al., (1999) *Transplant Proc* 31, 1224-1226.
Im, D. S. et al., (2000) *J Biol Chem* 275, 14281-14286.
Im, D. S. et al., Biochemistry 40, 2001, 14053-14060.
Jones, L. et al., (1997) *J Org Chem* 62, 1388-1410.
Kaiser, C. et al., XP009032189, Nov. 1962, 1243-1265.
Kawasaki, K. et al., *Tetrahedron*, vol. 53, No. 18, 1997, 6337-6350.
Kharel, Y. et al., *J Bio Chem*, vol. 280, No. 44, Nov. 4, 2005, 36865-36872.
Kimura, T. et al., (2003) *Arterioscler Thromb Vasc Biol* 23, 1283-1288.
Kiuchi, M. et al.,(2000) *J Med Chem* 43, 2946-2961.
Kon, J. et al., (1999) *J Biol Chem* 274, 23940-23947.
Kotera et al. Chem. Abst.: Registry Record 19352-04-6, 1968.
Lee, M. J. et al., (1998) *Science* 279, 1552-1555.
Lew, M. J. et al., "Analysis of competitive agonist-antagonist interactions by nonlinear regression", (1995) *Trends Pharmacol Sci* 16, 328-337.
Li, Z. et al., *Journal of Medicinal Chemistry*, vol. 48, No. 20, Oct. 6, 2005, 6169-6173.
Maki, T. et al., (2002) *Transplantation* 74, 1684-1686.
Maki, T. et al., (2005) *Transplantation* 79, 1051-1055.
Mandala, S. et al., (2002) *Science* 296, 346-349.
Matloubian, M. et al., (2004) *Nature* 427, 355-360.
Sanchez, T. et al., (2003) *J Biol Chem* 278, 47281-47290.
Sanna, M. G. et al., (2004) *J Biol Chem* 279, 13839-13848.
Sanna, M. G. et al., *Nature Chemical Biology*, vol. 2, Aug. 2006, 434-441.
Suzuki, S. et al., (1996) *Transpl Immunol* 4, 252-255.
Van Brocklyn, J. R. et al., (1999) *J Biol Chem* 274, 4626-4632.
Vogler, R. et al., (2005), No. 20, 2005, 6169-6173.
Xie, J. H. et al., (2003) *J Immunol* 170, 3662-3670.
Yanagawa, Y. et al., (2000) *Int J Immunopharmacol* 22, 597-602.
Yanagawa, Y. et al., (1999) *Transplant Proc* 31, 1227-1229.
Yang, Z., et al., (2003) *Clin Immunol* 107, 30-35.
Zhang, T. et al., (1997) *Cancer Res* 57, 169-175.
Zhang, Y. H. et al., *J Neurophysiol* 96, 2006, 1042-1052.
Zhang, Y. H. et al., *J Physiol* 575.1, 2006, 101-113.
"European Application Serial. No. 07868830.6, Office Action mailed on Mar. 3, 2011", 5 pgs.
Clemens, J. J, et al., "Synthesis of benzimidazole based analogues of sphingosine-1- phosphate: discovery of potent, subtype-selective S1P4 receptor agonists", Bioorg Med Chem Lett., 14(19), (Oct. 4, 2004), 4903-6.

* cited by examiner

FTY720

AAL151

XXIX

Scheme 1

Scheme 1. (i) 1-octene, 9-BBN, THF. (ii) Product of i, 5-bromo-1-indanone, THF, NaOH, Pd(Ph$_3$)$_4$, 95%. (iii) Br$_2$, CHCl$_3$, 84%. (iv) Diethyl acetamidomalonate, NaH, DMF, 65%. (v) Et$_3$SiH, TiCl$_4$, CH$_2$Cl$_2$, 72% . (vi) LiBH$_4$, THF, 10%. (vii) MeOH, LiOH, 37% .

Scheme 2

(i) 12M HCl, MeOH, reflux, 46% . (ii) LAH, THF, reflux .

Scheme 3

Scheme 4

2,5-Hydrindane and Unsaturated 2,5-Hydrindane Compounds

Scheme 5

2,5-Hydrindane Hetero Compounds

X, e.g., is O, S, NH, NR', NC(O)R"

Scheme 6

HYDRINDANE ANALOGS HAVING SPHINGOSINE 1-PHOSPHATE RECEPTOR AGONIST ACTIVITY

CROSS-REFERENCE TO RELATED APPLICATIONS

This application is a continuation of International Application PCT/US2007/085401, filed on Nov. 21, 2007, and published in English as WO 2008/064320 on May 29, 2008, which claims priority from Provisional Application Nos. 60/956,378, filed Aug. 16, 2007 and Application Ser. No. 60/860,697, filed Nov. 21, 2006, the disclosures of all of which are herein incorporated by reference in their entirety.

US GOVERNMENT RIGHTS

This invention is made with United States Government support under Grant No. RO1 GM 067958 awarded by the National Institutes of Health. The United States Government has certain rights in the invention.

BACKGROUND OF THE INVENTION

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl)ethyl]propane 1,3-diol), that following phosphorylation, is an agonist at 4 of 5 S1P receptors, revealed that enhancing S1P tone influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds.

Sphingosine 1-phosphate (S1P) is a lysophospholipid mediator that evokes a variety of cellular responses by stimulation of five members of the endothelial cell differentiation gene (EDG) receptor family.

Sphingosine-1-phosphate (S1P) has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing and tumor growth inhibition.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine 1-phosphate phosphohydrolases. Irreversible degradation of S1P is catalyzed by S1P lyase yielding ethanolamine phosphate and hexadecenal.

Currently, there is a need for novel, potent, and selective agents that are agonists of the S1P receptor having enhanced potency, selectivity, and oral bioavailability. In addition, there is a need in the art for identification of, as well as the synthesis and use of such compounds. The present invention satisfies these needs.

SUMMARY

The present invention provides in one aspect compounds that have agonist activity at one or more of the S1P receptors. The compounds are sphingosine analogs which, after phosphorylation, can behave as agonists at S1P receptors. Accordingly, there is provided compounds of Formula IA or IB:

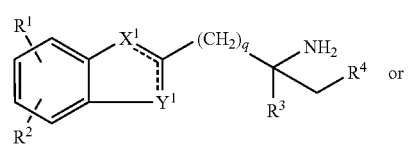

IA

-continued

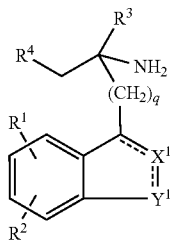

wherein $X^1$, and $Y^1$ are independently O, $CR^a$, $CR^aR^b$, N, $NR^c$, or S;

$R^1$ and $R^2$ are independently hydrogen, halo, halo($C_1$-$C_{10}$)alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl; or $R^2$ can be a group having Formula II, III, IV, V, or VI:

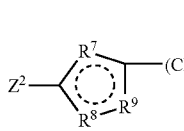

II

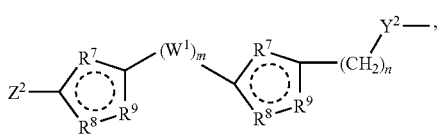

III

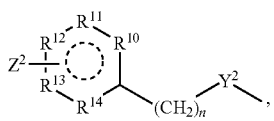

IV

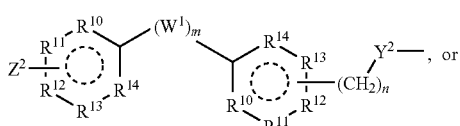

V

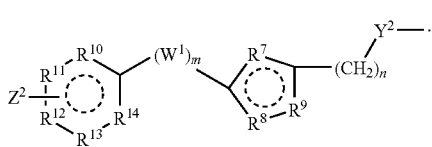

VI wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{13}$; and each $R^{15}$, $R^{16}$ and $R^{17}$ is independently hydrogen, halo, ($C_1$-$C_{10}$)alkyl, ($C_6$-$C_{10}$)aryl, ($C_1$-$C_{10}$)alkyl substituted with halo, hydroxy, ($C_1$-$C_{10}$)alkoxy, or cyano; and where $R^{18}$ can be hydrogen or ($C_1$-$C_{10}$)alkyl;

$Z^2$ is hydrogen, halo, halo($C_1$-$C_{10}$)alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl. The alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $Z^2$ alkyl groups can be independently replaced with non-peroxide oxygen, sulfur or $NR^c$; ⌒ indicates one or more optional double bonds; $Y^2$ is a bond (absent), O, S, C=O, or $NR^c$, $CH_2$; $W^1$ is a bond; —$CH_2$— and m is 1, 2, or 3, or (C=O)($CH_2$)$_{1-5}$ and m is 1; wherein $W^1$ is optionally interrupted with non-peroxide O, S, C=O, or $NR^c$. Each ---represents an optional double bond; and n is 0, 1, 2, or 3, and q is 0, 1, 2, or 3.

$R^3$ is hydrogen, ($C_1$-$C_{10}$)alkyl, hydroxy($C_1$-$C_{10}$)alkyl or ($C_1$-$C_{10}$)alkoxy; and $R^4$ is hydroxy (—OH), phosphate (—$OPO_3H_2$), phosphonate (—$CH_2PO_3H_2$), or alpha-substituted phosphonate; $R^c$ is hydrogen, or ($C_1$-$C_{10}$)alkyl. Each $R^a$, $R^b$, $R^c$, and $R^d$ is independently hydrogen, or ($C_1$-$C_{10}$)alkyl.

The alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $R^1$ or $R^2$ alkyl groups can be independently replaced with non-peroxide oxygen, sulfur or $NR^c$. The alkyl groups of $R^3$ are optionally substituted with 1, or 2 hydroxy groups; provided that in compounds having formula IA one of $X^1$ or $Y^1$ is $CR^a$ or $CR^aR^b$. The invention includes pharmaceutically acceptable salts or esters of the compounds of Formula IA or IB.

In another aspect, the invention provides phosphate monoesters having formula VIIIA or VIIIB:

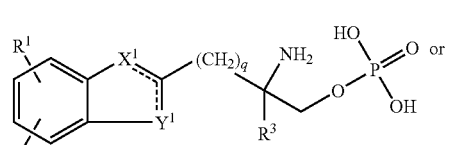

VIIIA

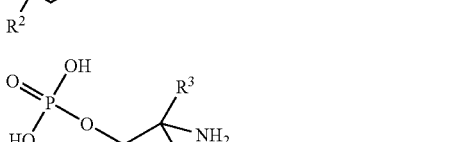

VIIIB

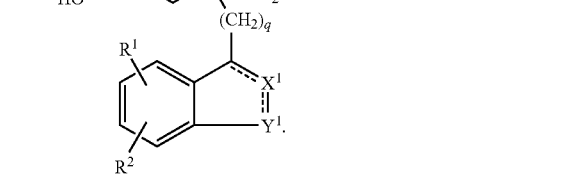

where $R^1$, $R^2$, $R^3$, $R^4$, $X^1$, $Y^1$ and q are as defined above.

In another aspect, the invention provides pro-drugs of the compounds of Formula IA or IB. The invention also provides pharmaceutically acceptable salts or esters of compounds of Formula IA or IB for use in medical therapy.

In another aspect, the present invention provides a method for inhibiting angiogenesis in a tumor, including contacting the cancerous cells with an effective amount of a compound of Formula IA or IB, or a pharmaceutically acceptable salt or ester thereof.

In another aspect, the invention provides a method for modulating the immune system by altering lymphocyte trafficking for treatment of autoimmune diseases or prolongation of allograft transplant survival, said method includes administering to a subject in need thereof an effective amount of at least one compound of Formula IA or IB, or a pharmaceutically acceptable salt or ester thereof.

In another aspect, the invention provides a method for preventing, inhibiting or treating neuropathic pain, wherein the method comprises administering an effective amount of at least one compound of Formula IA or IB or a compound of Formula IA or IB and a pharmaceutically-acceptable carrier is administered to a subject in need thereof. Pain can be nociceptive or neuropathic in nature.

Neuropathic pain is characterized by its chronic nature, an absence of an obvious, direct cause (e.g., tissue damage), hyperalgesia or allodynia. Hyperalgesia is an exaggerated response to a painful stimulus. Allodynia is the perception of normal stimuli as painful (examples include the touch of clothing, warm or cool air, etc.). Neuropathic pain can be a sequel to nerve damage in an extremity such as an arm, or more often a leg. Precipitating events can include trauma, e.g., motor vehicle accidents or amputations (e.g., phantom limb pain). Neuropathic pain can occur due to an adverse effect of drug therapies, e.g., vincristine or paclitaxel (TAXOL™) or can occur as a component of disease pathologies, such as diabetes type 1 or type 2, shingles, HIV-1 infections, etc. Typically, neuropathic pain is not responsive to opiates or non-steroidal anti-inflammatory drugs such as aspirin.

In another aspect, the invention provides a method for repairing a vascular injury following catheterization, including contacting the lumen of the affected vessel with an effective amount of the compound of Formula IA or IB. In another aspect, the invention includes coating indwelling stents with a compound of Formula IA or IB.

In another aspect, the present invention provides compositions and methods for the use of S1P analogs to prevent and inhibit vascular restenosis following vascular injury. For example, the injury can be due to balloon angioplasty. In another aspect, the present invention includes a method for treating subjects to prevent vascular restenosis.

In another aspect, the present invention provides compositions and methods for the use of sphingosine analogs (including S1P pro-drugs) to prevent asthma attacks. In one aspect, the asthma could be due to over production of cysteinyl leukotrienes. In another aspect, the present invention includes a method for treating subjects to treat asthma.

In another aspect, the present invention provides compositions and methods for the use of sphingosine analogs of Formula IA or IB (including S1P pro-drugs) to treat obesity.

In another aspect, the present invention provides compositions and methods for the use of sphingosine analogs (including S1P pro-drugs) to normalize blood lipid composition. In one aspect, blood low density lipoprotein (LDL or 'bad cholesterol') levels could be lowered. In another aspect, blood triglyceride levels could be lowered.

In another aspect, the present invention provides compositions and methods for the use of S1P analogs and S1P pro-drugs for the prevention and treatment of arteriosclerosis.

In another aspect, the present invention provides compositions and methods for the use of S1P analogs and S1P pro-drugs for the treatment of neoplastic disease. In one aspect, this treatment is effected by application of S1P receptor antagonists that are efficacious by virtue of their anti-angiogenic properties. In another aspect, the treatment is effected by administration of sphingosine analogs of Formula IA or IB that inhibit the multiple substrate lipid kinase.

In another aspect, the present invention provides compositions and methods for the use of S1P analogs and S1P pro-drugs for the treatment of neurodegenerative diseases. In one aspect, the treatment is for senile dementia of the Alzheimers type.

In another aspect, the invention provides a compound of Formula IA or IB, a pharmaceutically acceptable salt or ester thereof for use in medical treatment (for example, treatment of neoplastic disease, treatment of neuropathic pain, treatment of autoimmune disease, prolongation of allograft survival).

In another aspect, the invention provides a method for the use of a compound of Formula IA or IB or a pharmaceutically acceptable salt or ester thereof to prepare a medicament for inhibiting tumor growth, metastasis or tumor angiogenesis in a mammalian species (for example, a human).

In another aspect, the invention provides for the use of a compound of Formula IA or IB or a pharmaceutically acceptable salt or ester thereof to prepare a medicament for treating an autoimmune disease or prolonging allograft survival in a mammalian species (for example, a human).

In another aspect, the invention provides for the use of a compound of Formula IA or IB or a pharmaceutically acceptable salt thereof to prepare a medicament for treating neuropathic pain in a mammalian species (for example, a human).

In another aspect, the invention provides a method for assessing a compound of Formula IA or IB (e.g., S1P receptor pro-drugs) as a substrate for sphingosine kinase types 1 or 2, in vitro and in vivo. In another aspect, the invention includes a method of assessing a compound of Formula IA or IB for binding to designated receptor sites including in vivo or in vitro, with an amount of a compound of Formula IA or IB effective to bind said receptors. Tissue having ligand bound designated S1P receptor sites can be used to measure the selectivity of test compounds for specific receptor subtypes, or can be used as a tool to identify potential therapeutic agents for the treatment of diseases, by contacting said agents with said ligand-receptor complexes, and measuring the extent of displacement of the ligand or binding of the agent.

In another aspect, the invention provides novel intermediates and processes disclosed herein that are useful for preparing compounds of Formula IA or IB, including the generic and specific intermediates as well as the synthetic processes described herein.

In another aspect, the present invention provides synthetic schemes and methods of use of compounds having Formula IA or IB and analogs or derivatives thereof. In another aspect, the invention provides synthetic and modification schemes for preparing analogs and derivatives of the compounds of Formula IA or IB, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

DETAILED DESCRIPTION

Figure 1:
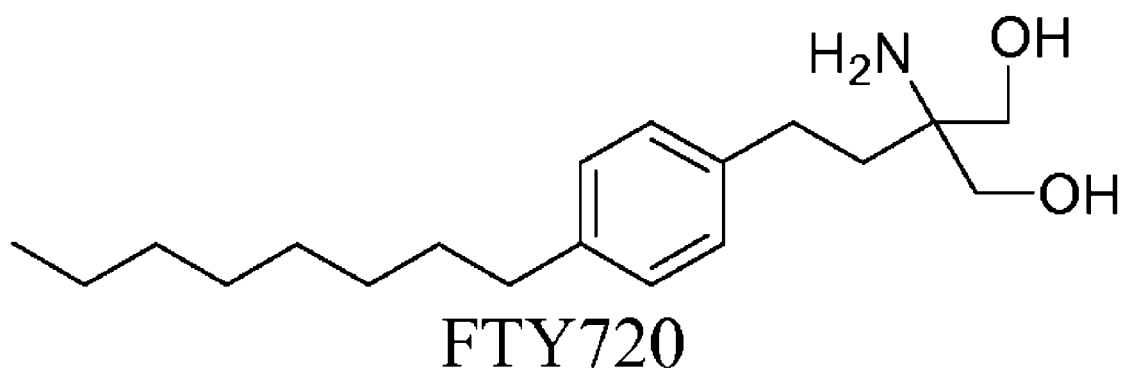
FIG. 1 illustrate three S1P agonists FTY720, AAL151 and compound XXIX.
Figure 1:
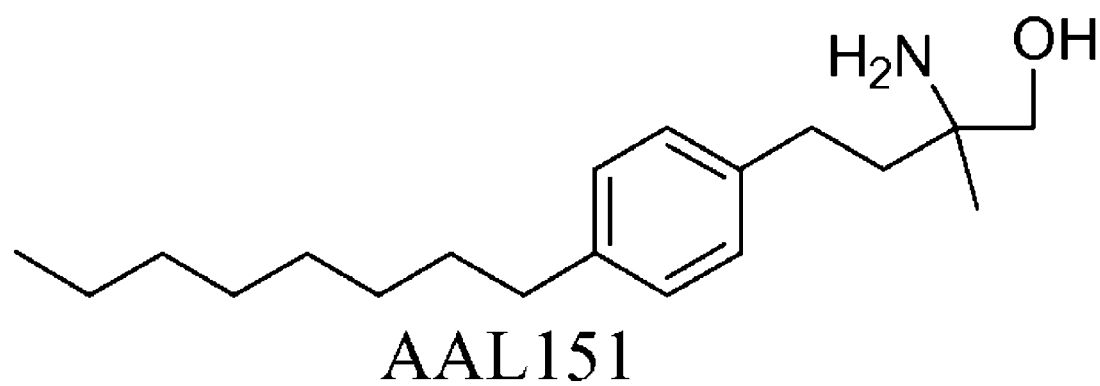
Figure 1:
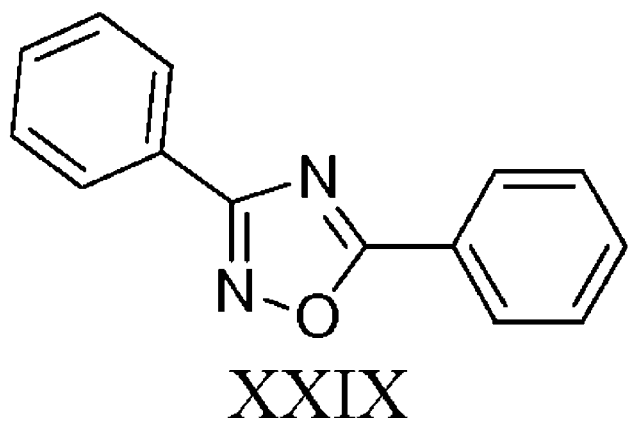
Figure 2A:
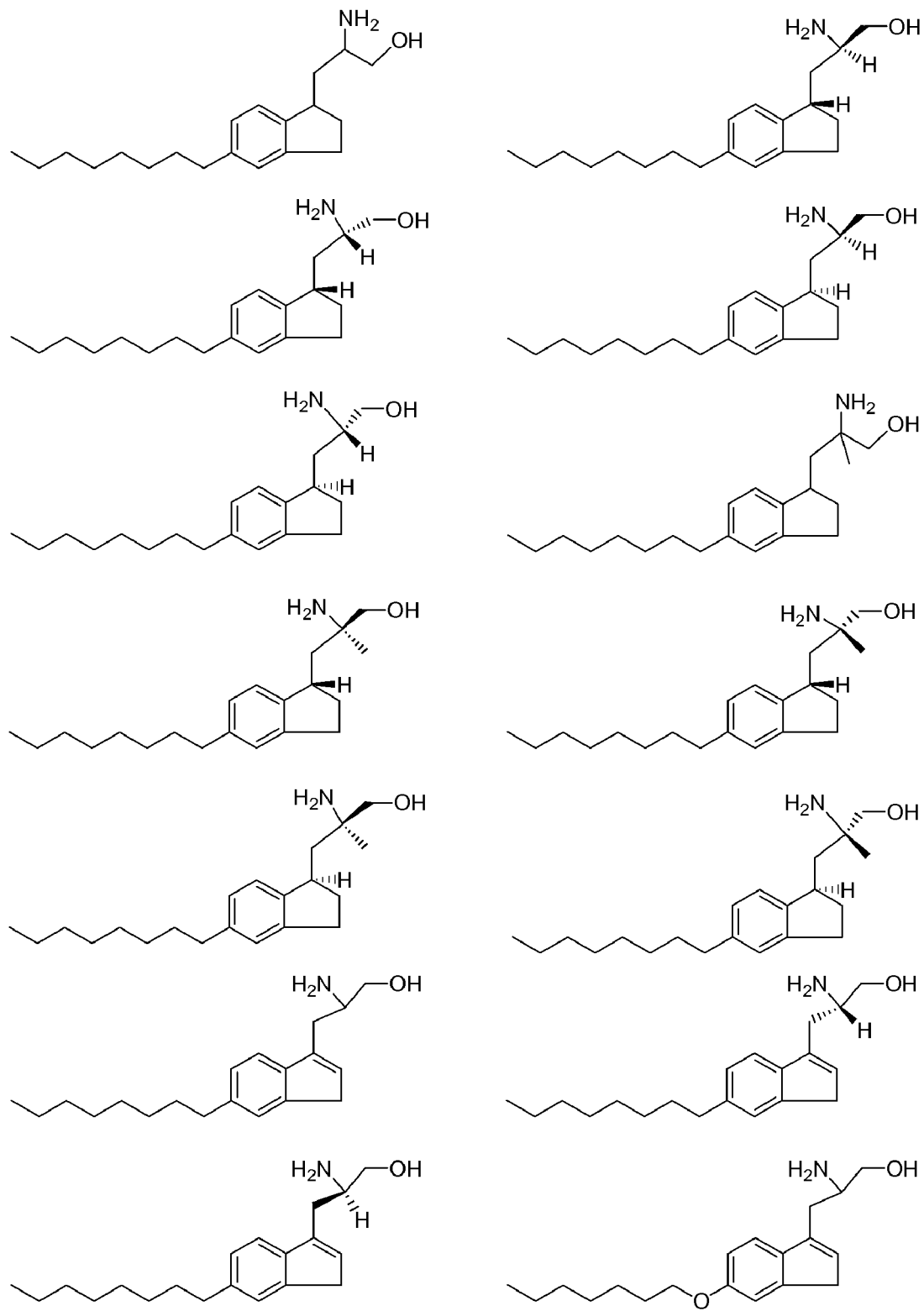
FIGS. 2A-2D illustrate additional compounds of Formula IA or IB.
Figure 2B:
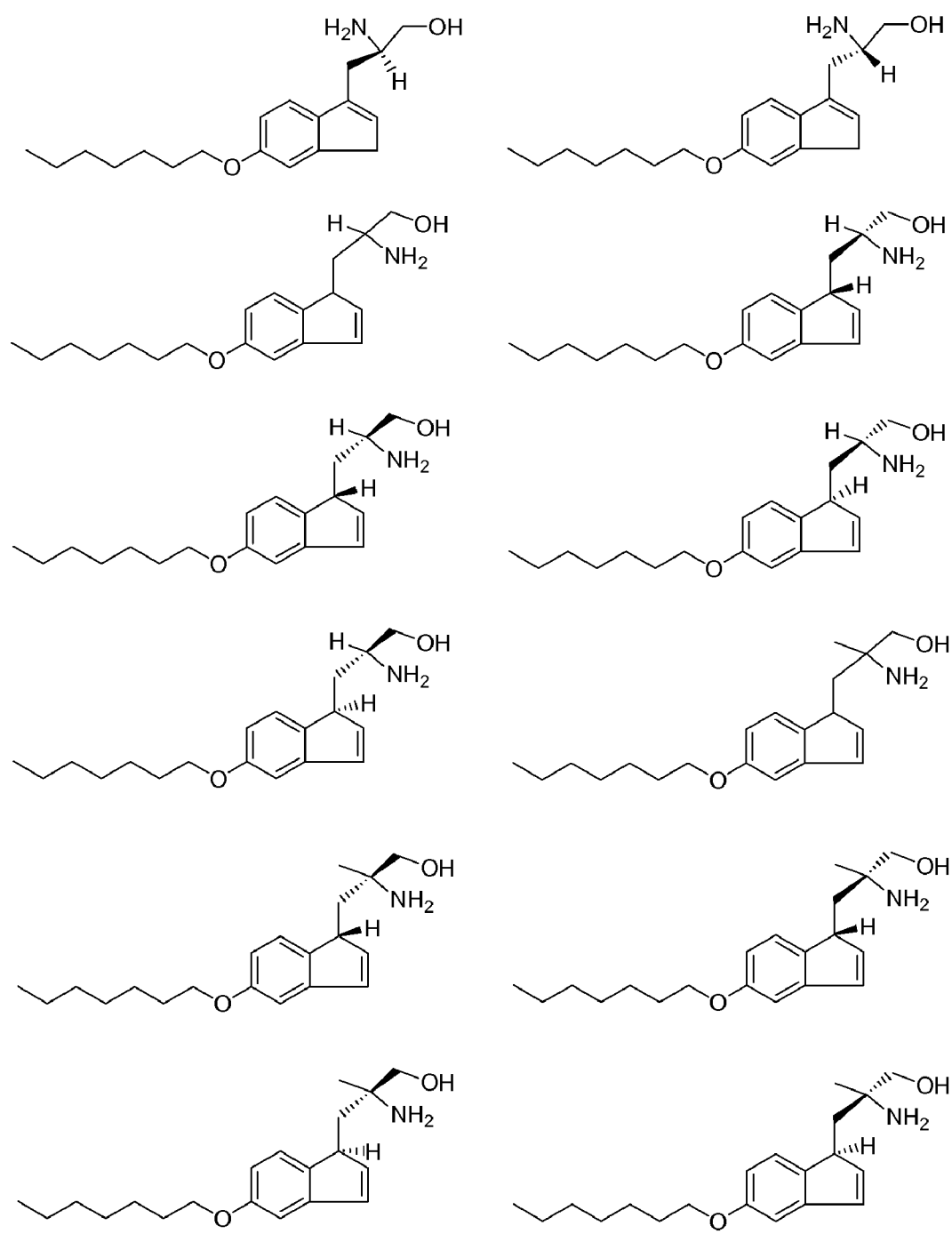
Figure 2C:
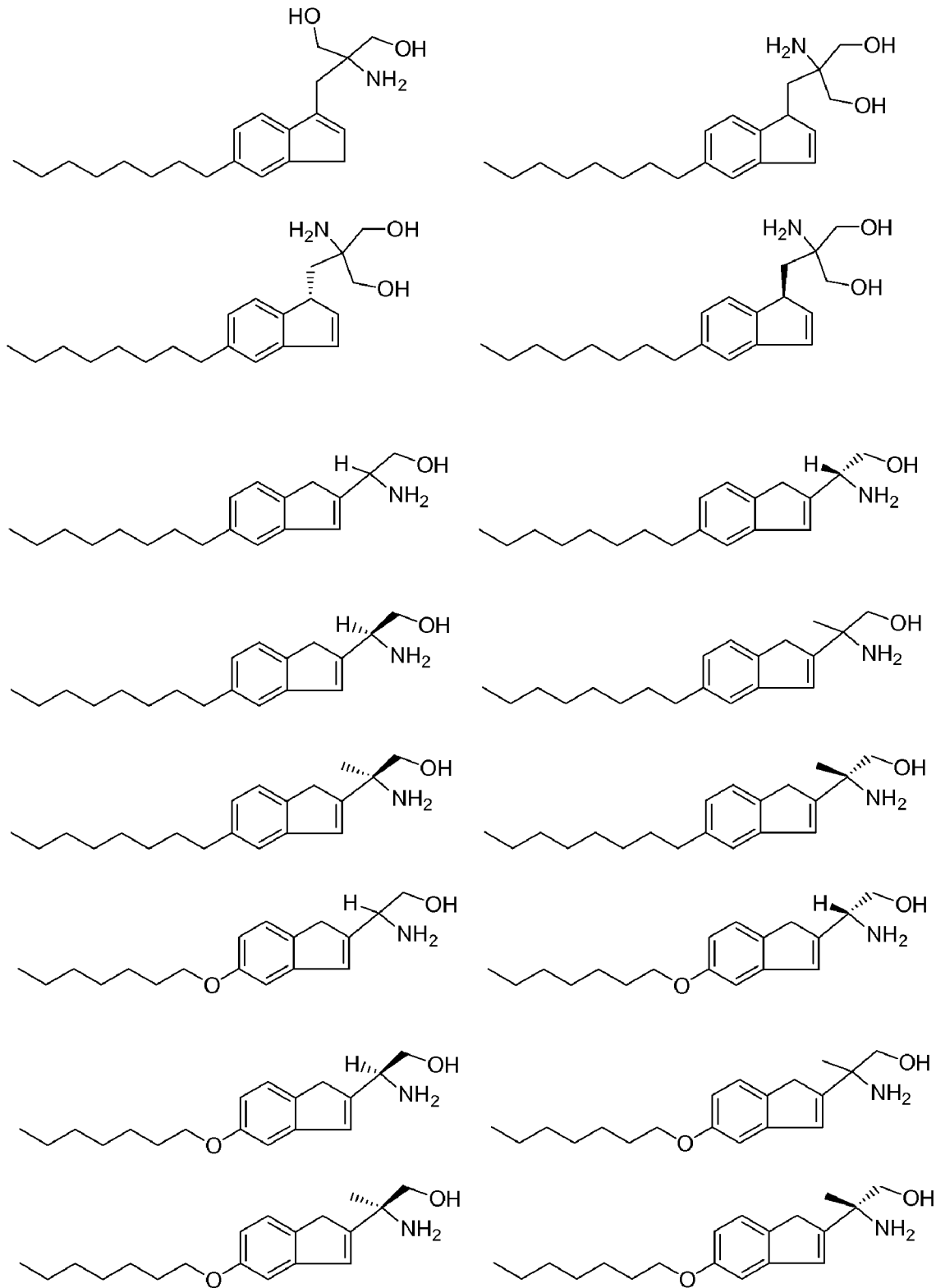
Figure 2D:
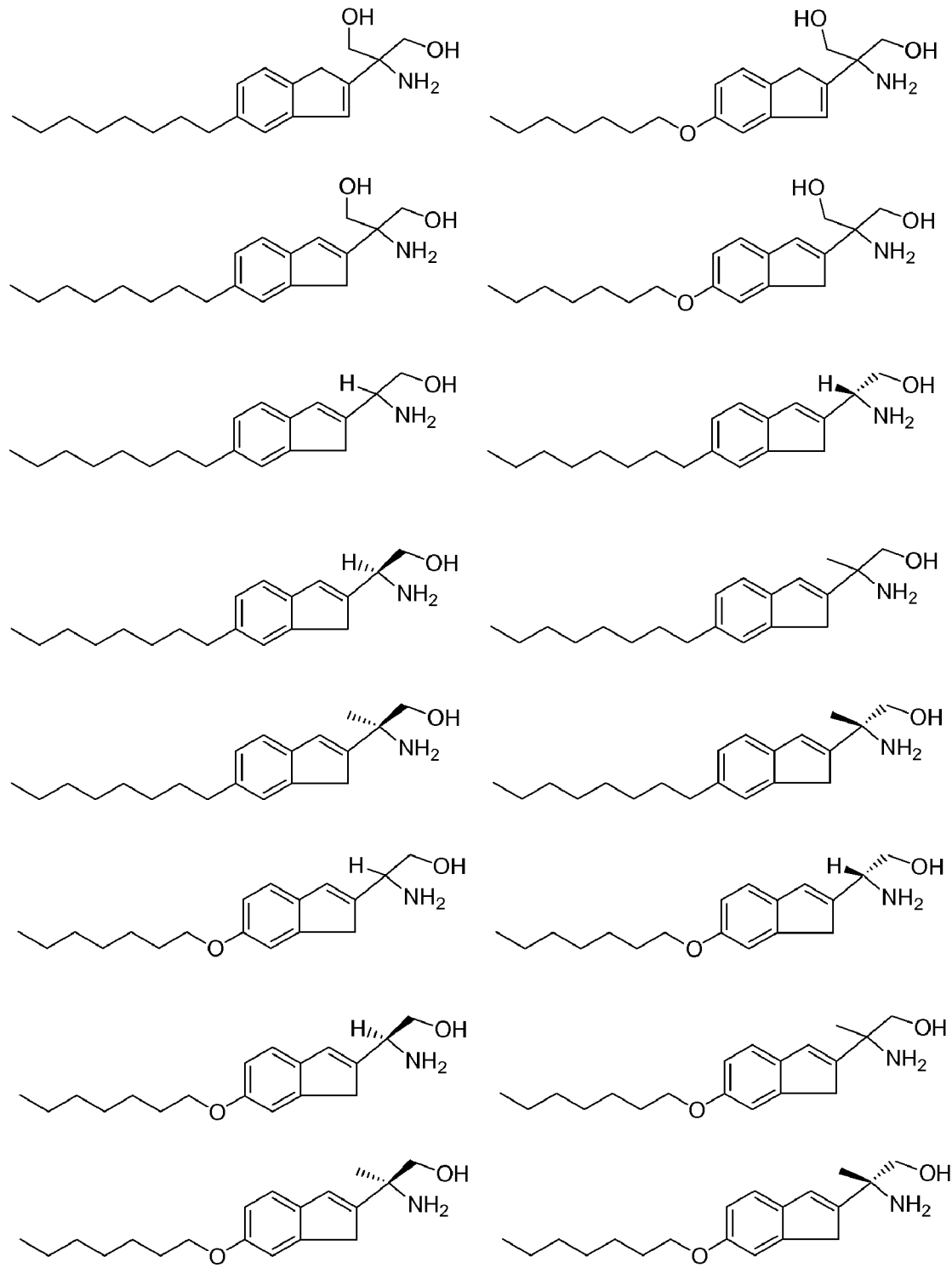

The following abbreviations are used herein: S1P, sphingosine-1-phosphate; $S1P_{1-5}$-S1P receptor types; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction.

In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Exemplary and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "receptor agonists" are compounds that mimic the action of S1P at one or more of its receptors but may have differing potency and/or efficacy.

The term "receptor antagonists" are compounds that 1) lack intrinsic agonist activity and 2) block agonist (e.g., S1P) activation of the S1P receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue is obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an S1P receptor antagonist is an amount that decreases the cell signaling activity of the S1P receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Preferably, inhibition is by at least 10%, more preferably by at least 25%, even more preferably by at least 50%, and most preferably, the function is inhibited by at least 75%.

"Instructional material" includes a publication, a recording, a diagram, or any other medium of expression which can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "rt" for room temperature, "THF" for tetrahydrofuran, and "rac" for racemic mixture).

The values listed below for radicals, substituents, and ranges, are for illustration only; they do not exclude other defined values or other values within defined ranges for the radicals and substituents. The disclosed compounds include compounds of Formula IA, IB, or IC having any combination of the exemplary values, preferred values, and more preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like. The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The term "($C_1$-$C_{20}$)alkoxy" refers to an alkyl group attached through an oxygen atom. Examples of ($C_1$-$C_{20}$)alkoxy can be methoxy, ethoxy, propoxy, isopropoxy, butoxy, iso-butoxy, sec-butoxy, pentoxy, 3-pentoxy, hexyloxy, heptoxy, or octoxy and the like. The term ($C_2$-$C_{26}$)alkoxyalkyl can be methoxy methyl, methoxy ethyl, ethoxy methyl, ethoxy ethyl, and the like.

The term "$C_3$-$C_{12}$ cycloalkyl", can be cyclopropyl, cyclobutyl, cyclopentyl, cyclohexyl, cycloheptyl, cyclooctyl and the like.

The term "optionally substituted" refers to zero, one, two, three or four substituents, wherein the substituents are each independently selected. Each of the independently selected substituents may be the same or different than other substituents.

The term "($C_6$-$C_{10}$)aryl" refers to a mono or bicyclic carbocyclic ring system having one or two aromatic rings including, but not limited to, phenyl, benzyl, naphthyl, tetrahydronaphthyl, indanyl, indenyl, and the like.

The term "aryl($C_1$-$C_{20}$)alkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, or amino substituents.

The "($C_2$-$C_{10}$)heterocyclic group" refers to an optionally substituted mono- or bicyclic carbocyclic ring system containing one, two, or three heteroatoms (optionally in each ring) wherein the heteroatoms are oxygen, sulfur, and nitrogen.

The term "($C_4$-$C_{10}$)heteroaryl" refers to an optionally substituted mono- or bicyclic carbocyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "bicyclic" represents either an unsaturated or saturated stable bridged or fused bicyclic carbon ring. The bicyclic ring may be attached at any carbon atom which affords a stable structure. Typically a bicyclic ring system can have from about 7 to about 12 atoms in the ring system. The term includes, but is not limited to, naphthyl, dicyclohexyl, dicyclohexenyl, and the like.

The term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, K, and the like if such counterions are present.

The term "alpha-substituted phosphonate" includes phosphonate ($-CH_2PO_3H_2$) groups that are substituted on the alpha-carbon such as $-CHFPO_3H_2$, $-CF_2PO_3H_2$, $-CHOHPO_3H_2$, $-C=OPO_3H_2$) and the like.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

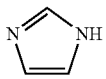

is understood to represent a mixture of the structures:

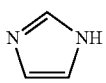

as well as

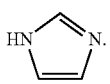

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, and $S1P_5$), unless the specific subtype is indicated.

The disclosed compounds can contain one or more asymmetric centers in the molecule. In accordance with the present disclosure any structure that does not designate the stereochemistry is to be understood as embracing all the various optical isomers, as well as racemic mixtures thereof.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, resolution of the racemic form by recrystallization techniques, synthesis from optically-active starting materials, chiral synthesis, or by chromatographic separation using a chiral stationary phase) and how to determine S1P agonist activity using the standard tests described herein, or using other similar tests which are well known in the art. In addition, some compounds may exhibit polymorphism.

Potential uses of an S1P receptor agonist pro-drugs ($S1P_1$ receptor type selective agonists preferred) include, but are not limited to, altering lymphocyte trafficking as a method of treatment for autoimmune pathologies such as uveitis, type I diabetes, rheumatoid arthritis, inflammatory bowel diseases, and, most particularly, multiple sclerosis. "Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In addition, the disclosed compounds can be used for altering lymphocyte trafficking as a method for prolonging allograft survival, for example solid organ transplants, treatment of graft vs. host disease, bone marrow transplantation, and the like.

In addition, the disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs of the disclosed compounds can be used to inhibit autotaxin. This activity may be combined with agonism at S1P receptors or may be independent of such activity.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit S1P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

"Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In another aspect, the present invention provides compositions and methods for the use of the S1P analogs of the invention to prevent, inhibit, or treat neuropathic pain by agonizing or antagonizing the S1P receptors. Pain can be nociceptive or neuropathic in nature. Neuropathic pain is characterized by its chronic nature, an absence of an obvious, direct cause (i.e., tissue damage), and allodynia. Allodynia is the perception of normal stimuli as painful (examples include the touch of clothing, warm or cool air, etc.). Neuropathic pain is often a sequel to nerve damage in an extremity such as an arm, or more often, a leg. Typically, neuropathic pain is not responsive to opiates or non-steroidal anti-inflammatory drugs such as aspirin.

In another aspect, the present invention provides compositions and methods for the use of S1P analogs to prevent and inhibit vascular restenosis following vascular injury. In one aspect, the injury can be due to balloon angioplasty. The present invention further provides methods for treating subjects to prevent vascular restenosis.

In another aspect, the present invention provides compositions and methods for the use of sphingosine analogs (including S1P pro-drugs) to prevent asthma attacks. In one aspect, the asthma could be due to over production of cysteinyl leukotrienes. The present invention further provides methods for treating subjects to treat asthma.

In another aspect, the present invention provides compositions and methods for the use of sphingosine analogs (including S1P pro-drugs) to treat obesity.

In another aspect, the present invention provides compositions and methods for the use of sphingosine analogs (including S1P pro-drugs) to normalize blood lipid composition. In one aspect, blood low density lipoprotein (LDL or 'bad cholesterol') levels could be lowered. In another aspect, blood triglyceride levels could be lowered.

In another aspect, the present invention provides compositions and methods for the use of S1P analogs and S1P pro-drugs for the prevention and treatment of arteriosclerosis.

In another aspect, the present invention provides compositions and methods for the use of S1P analogs and S1P pro-drugs for the treatment of neoplastic disease. In one aspect, this treatment is effected by application of S1P receptor antagonists that are efficacious by virtue of their anti-angiogenic properties. In another aspect, the treatment is effected by administration of sphingosine analogs that inhibit the multiple substrate lipid kinase.

In another aspect, the present invention provides compositions and methods for the use of S1P analogs and S1P pro-drugs for the treatment of neurodegenerative diseases. In one aspect, the treatment is for senile dementia of the Alzheimers type.

The present invention also includes pharmaceutical compositions including the disclosed compounds. More particularly, such compounds can be formulated as pharmaceutical compositions using standard pharmaceutically acceptable carriers, fillers, solubilizing agents and stabilizers known to those skilled in the art. For example, a pharmaceutical composition including a disclosed compound, analog, derivative, or modification thereof, as described herein, is used to administer the appropriate compound to a subject.

The compounds of Formula IA and IB are useful for treating a disease or disorder including administering to a subject in need thereof of a therapeutically acceptable amount of a compound of Formula IA or IB, or a pharmaceutical composition comprising a therapeutically effective amount of a compound of Formula IA or IB, and a pharmaceutically-acceptable carrier.

The disclosed compounds and method are directed to sphingosine 1-phosphate (S1P) analogs that have activity as receptor agonists or antagonists at one or more S1P receptors, specifically the S1P, $S1P_4$ and $S1P_5$ receptor types. The disclosed compounds and method include both compounds that have a phosphate moiety as well as compounds with hydrolysis-resistant phosphate surrogates such as phosphonates, alpha-substituted phosphonates particularly where the alpha substitution is a halogen and phosphothionates.

Exemplary and preferred values listed below for radicals, substituents, and ranges, are for illustration only; they do not exclude other defined values or other values within defined ranges for the radicals and substituents.

Exemplary values for $X^1$ and $Y^1$ are independently O, CH, $CH_2$, $CHCF_3$, N, NH, or S.

Another exemplary value for $X^1$ or $Y^1$ is $CH_2$.

Exemplary compounds of the invention have formulas

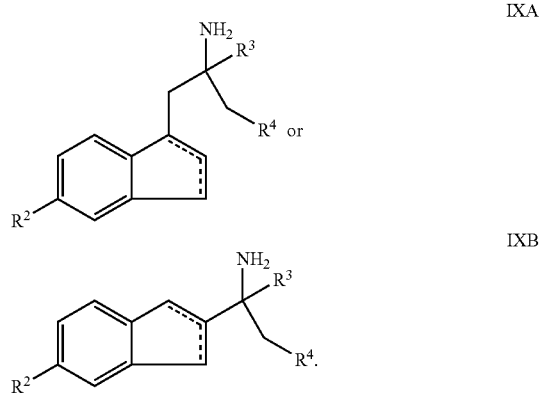

Values for $R^1$ are hydrogen, fluorine, chlorine, bromine, trifluoro-methyl, methoxy, $(C_1-C_6)$alkyl, $(C_1-C_6)$haloalkyl, or $(C_1-C_6)$alkyl substituted with, alkoxy or cyano.

More values for $R^1$ are hydrogen, trifluoro-methyl, or —$CH_2CF_3$.

Additional values for $R^1$ are alkyl-substituted aryl, aryl-substituted alkyl, or aryl-substituted arylalkyl.

Even more values for $R^1$ are benzyl, phenylethyl, or benzyl substituted with methyl.

Values for $R^2$ include

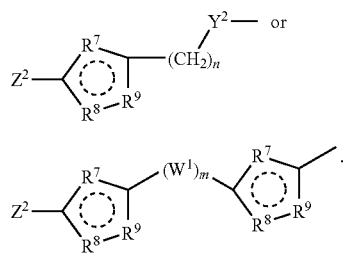

Additional values for $R^2$ having Formula VI are

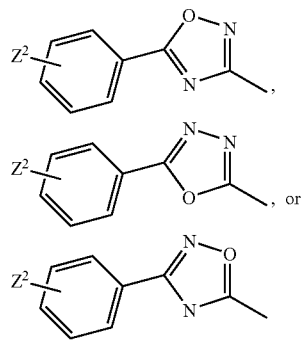

wherein $Z^2$ is $(CH_3)_3C-$, $CH_3CH_2(CH_3)_2C-$, $CH_3CH_2CH_2-$, $CH_3(CH_2)_2CH_2-$, $CH_3(CH_2)_4-CH_2-$, $(CH_3)_2CHCH_2-$, $(CH_3)_3CCH_2-$, $CH_3CH_2O-$, $(CH_3)_2CHO-$, or $CF_3CH_2CH_2-$ or a group having the formula:

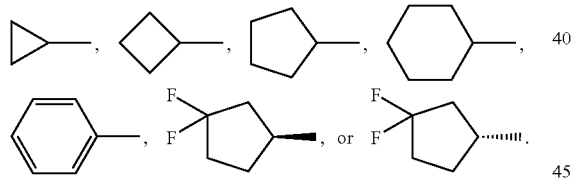

An additional value for $R^2$ having Formula VI (para substituted 3,5-diphenyl-(1,2,4)-oxadiazoles) is;

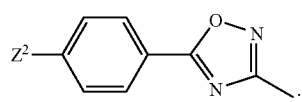

Another value for $R^2$ having Formula VI is;

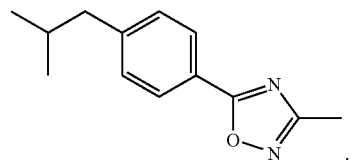

Another value for $R^2$ having Formula II is;

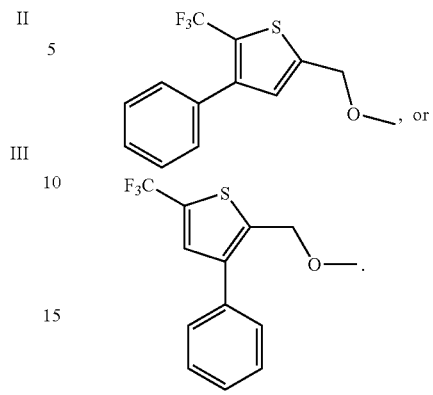

Another exemplary value for $R^2$ having Formula II is;

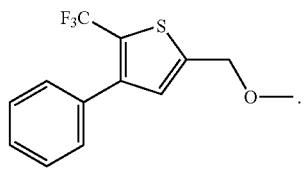

An exemplary values for $R^2$ having Formula III include;

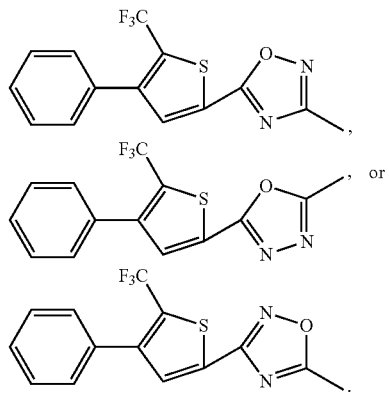

An exemplary value for $R^2$ having formula V is;

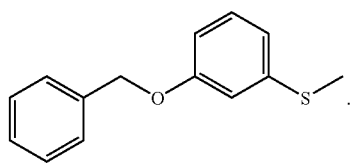

Additional values for $R^2$ include $(C_1-C_{20})$alkyl, $(C_1-C_{20})$alkoxy, or $(C_2-C_{26})$alkoxyalkyl.

More additional values for $R^2$ include $(C_1-C_{10})$alkyl, $(C_2-C_{10})$alkenyl and $(C_2-C_{14})$alkynyl or $(C_1-C_{10})$alkoxy optionally substituted with carbonyl (C=O) or oxime (C=NR$^d$) groups.

Additional values for $R^2$ include methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

Values for $R^3$ include methyl, hydroxymethyl, ethyl, hydroxyethyl, propyl, hydroxypropyl, or isopropyl.

Additional values for $R^3$ include methyl, hydroxymethyl, ethyl, or hydroxyethyl.

Values for $R^4$ include is hydroxy, or phosphate ($-OPO_3H_2$).

Additional Embodiments

Additional embodiments of the invention include:

1. A compound of Formula IA or IB:

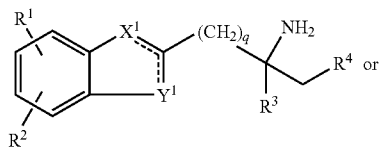

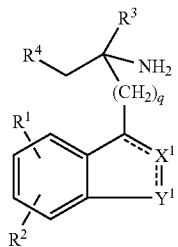

wherein $X^1$ and $Y^1$ are independently O, $CR^a$, $CR^aR^b$, N, $NR^c$, or S;

$R^1$ and $R^2$ are independently hydrogen, halo, halo($C_1$-$C_{10}$)alkyl, cyano, $-NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl;

wherein the alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $R^1$ or $R^2$ alkyl groups can be independently replaced with non-peroxide oxygen, sulfur or $NR^c$; and the alkyl groups of $R^3$ are optionally substituted with 1, or 2 hydroxy groups; or $R^2$ can be a group having formula II, III, IV, V, or VI;

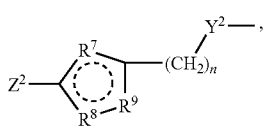

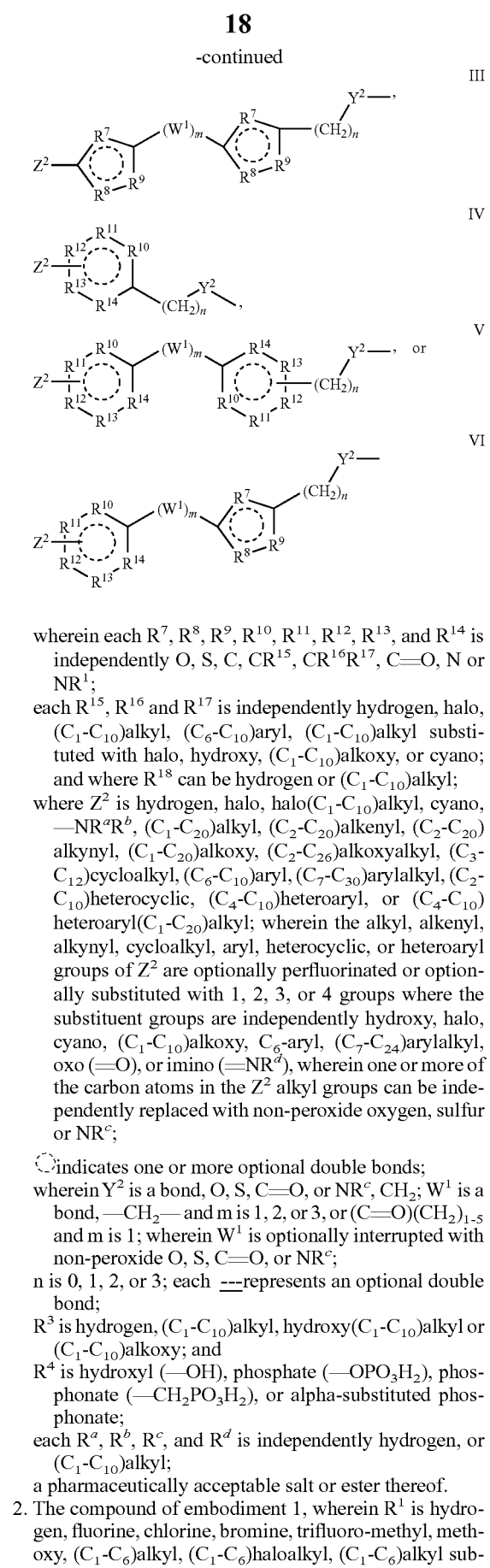

wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^1$;

each $R^{15}$, $R^{16}$ and $R^{17}$ is independently hydrogen, halo, ($C_1$-$C_{10}$)alkyl, ($C_6$-$C_{10}$)aryl, ($C_1$-$C_{10}$)alkyl substituted with halo, hydroxy, ($C_1$-$C_{10}$)alkoxy, or cyano; and where $R^{18}$ can be hydrogen or ($C_1$-$C_{10}$)alkyl;

where $Z^2$ is hydrogen, halo, halo($C_1$-$C_{10}$)alkyl, cyano, $-NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl; wherein the alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $Z^2$ alkyl groups can be independently replaced with non-peroxide oxygen, sulfur or $NR^c$;

⌢ indicates one or more optional double bonds;

wherein $Y^2$ is a bond, O, S, C=O, or $NR^c$, $CH_2$; $W^1$ is a bond, $-CH_2-$ and m is 1, 2, or 3, or (C=O)($CH_2$)$_{1-5}$ and m is 1; wherein $W^1$ is optionally interrupted with non-peroxide O, S, C=O, or $NR^c$;

n is 0, 1, 2, or 3; each --- represents an optional double bond;

$R^3$ is hydrogen, ($C_1$-$C_{10}$)alkyl, hydroxy($C_1$-$C_{10}$)alkyl or ($C_1$-$C_{10}$)alkoxy; and $R^4$ is hydroxyl ($-OH$), phosphate ($-OPO_3H_2$), phosphonate ($-CH_2PO_3H_2$), or alpha-substituted phosphonate;

each $R^a$, $R^b$, $R^c$, and $R^d$ is independently hydrogen, or ($C_1$-$C_{10}$)alkyl;

a pharmaceutically acceptable salt or ester thereof.

2. The compound of embodiment 1, wherein $R^1$ is hydrogen, fluorine, chlorine, bromine, trifluoro-methyl, methoxy, ($C_1$-$C_6$)alkyl, ($C_1$-$C_6$)haloalkyl, ($C_1$-$C_6$)alkyl substituted with, alkoxy or cyano, alkyl-substituted aryl, aryl-substituted alkyl, or aryl-substituted arylalkyl.

3. The compound of embodiment 2, wherein $R^1$ is hydrogen, trifluoro-methyl, or —$CH_2CF_3$.

4. The compound of embodiment 2, wherein $R^1$ is benzyl, phenylethyl, or benzyl substituted with methyl.

5. The compound of any of embodiments 1-4, wherein $R^2$ is

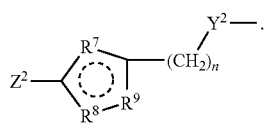

6. The compound of embodiment 5, wherein $R^2$ is:

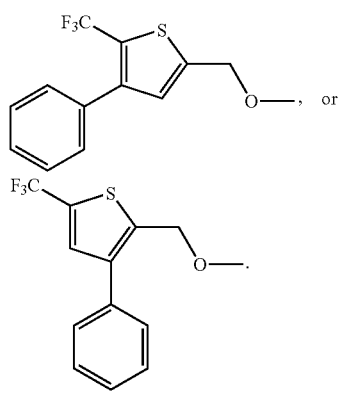

7. The compound of embodiment 6, wherein $R^2$ is

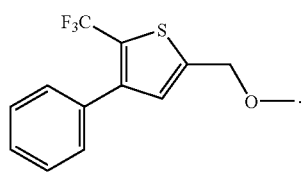

8. The compound of any of embodiments 1-4, wherein $R^2$ is:

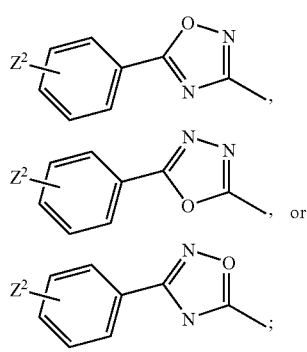

wherein $Z^2$ is $(CH_3)_3C$—, $CH_3CH_2(CH_3)_2C$—, $CH_3CH_2CH_2$—, $CH_3(CH_2)_2CH_2$—, $CH_3(CH_2)_4$—$CH_2$—, $(CH_3)_2CHCH_2$—, $(CH_3)_3CCH_2$—, $CH_3CH_2O$—, $(CH_3)_2CHO$—, or $CF_3CH_2CH_2$— or a group having the formula:

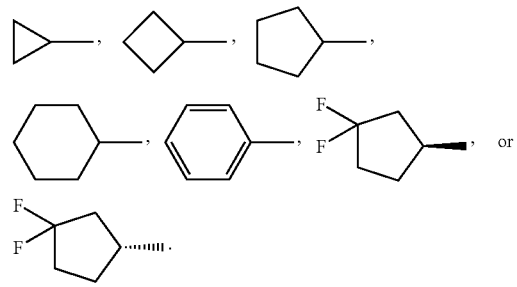

9. The compound of embodiment 8, wherein $R^2$ is:

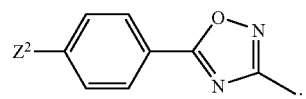

10. The compound of embodiment 9, wherein $R^2$ is:

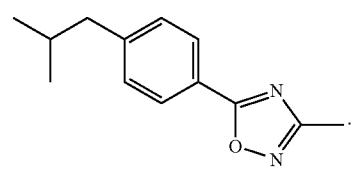

11. The compound of any of embodiments 1-4, wherein $R^2$ is

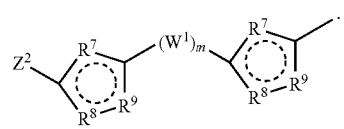

12. The compound of embodiment 11, wherein $R^2$ is

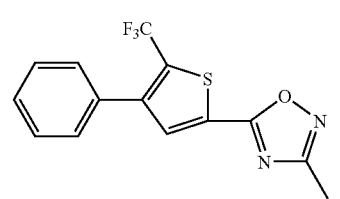

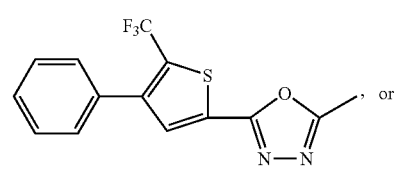

-continued

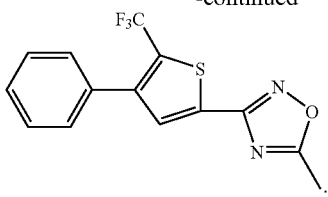

13. The compound of any of embodiments 1-4, wherein $R^2$ is $(C_1-C_{20})$alkyl, or $(C_1-C_{20})$alkoxy.
14. The compound of embodiment 13, wherein $R^2$ is $(C_1-C_{10})$alkyl, $(C_2-C_{10})$alkenyl and $(C_2-C_{14})$alkynyl or $(C_1-C_{10})$alkoxy optionally substituted with carbonyl (C=O) or oxime (C=NR$^d$) groups.
15. The compound of embodiment 14, wherein $R^2$ is methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.
16. The compound of any of embodiments 1-15, wherein $X^1$ and $Y^1$ are both $CH_2$.
17. The compound of any of embodiments 1-16, wherein $R^3$ is hydrogen, methyl, hydroxymethyl, ethyl, hydroxyethyl, propyl, or isopropyl.
18. The compound of embodiment 17, wherein $R^3$ is hydrogen, methyl, hydroxymethyl, ethyl, or hydroxyethyl.
19. The compound of any of embodiments 1-18 having the formula

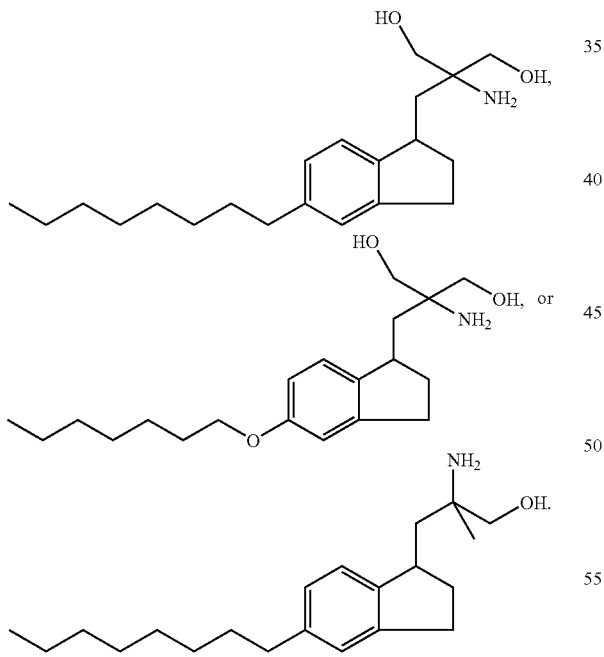

20. A method for prevention or treatment of a pathological condition or symptom in a mammal, wherein the activity of sphingosine 1-phosphate receptors is implicated and agonism of such activity is desired, comprising administering to said mammal an effective amount of a compound of any of embodiments 1-19.
21. The method of embodiment 19, wherein the pathological condition is an autoimmune disease.
22. The method of embodiment 21, wherein the autoimmune disease is uveitis, type I diabetes, rheumatoid arthritis, inflammatory bowel diseases, or multiple sclerosis.
23. The method of embodiment 22, wherein the autoimmune disease is multiple sclerosis.
24. The method of embodiment 23, wherein the pathological condition is altering lymphocyte trafficking.
25. The method of embodiment 24, wherein the treatment is altering of lymphocyte trafficking.
26. The method of embodiment 25, wherein lymphocyte trafficking provides prolonged allograft survival.
27. The method of embodiment 26, wherein the allograft is for transplantation.
28. A method for prevention or treatment of a pathological condition or symptom in a mammal, wherein the activity S1P lyase implicated and inhibition of the S1P lyase is desired, comprising administering to said mammal an effective amount of a compound of any of embodiments 1-19.
29. A compound of any of embodiments 1-19 for use in medical therapy.
30. Use of a compound of any of embodiments 1-19 to prepare a medicament useful for prevention or treatment of a pathological condition or symptom in a mammal, wherein the activity of sphingosine 1-phosphate receptors is implicated.
31. The use of embodiment 30, wherein the medicament comprises a carrier.
32. The use of embodiment 31, wherein the carrier is a liquid.

Exemplary compounds of the invention have formulas

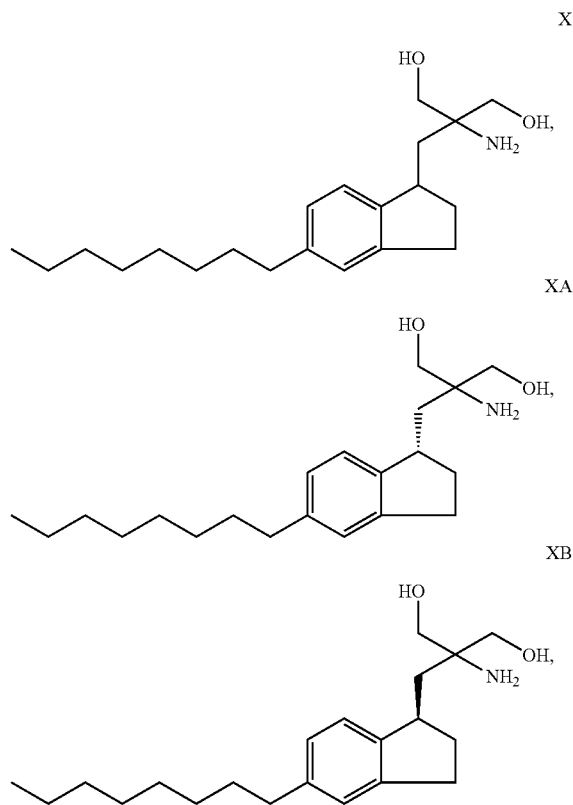

XI
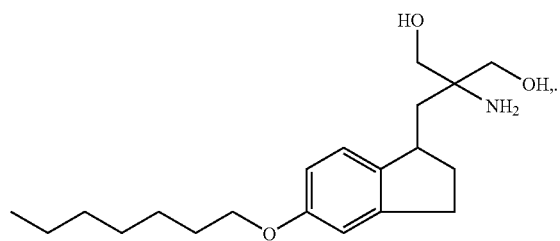
XIA
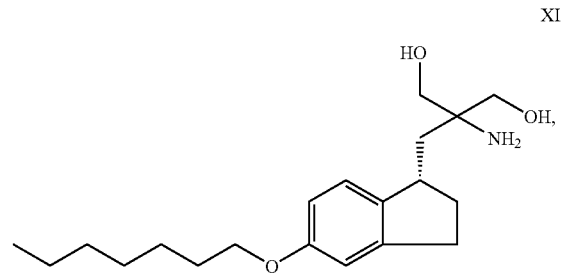
XIB
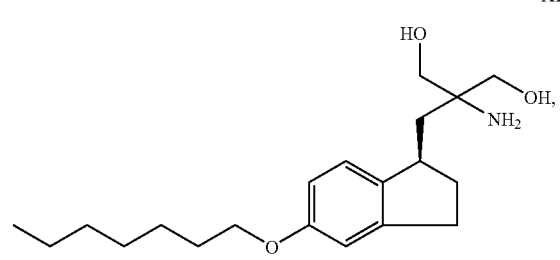
XII
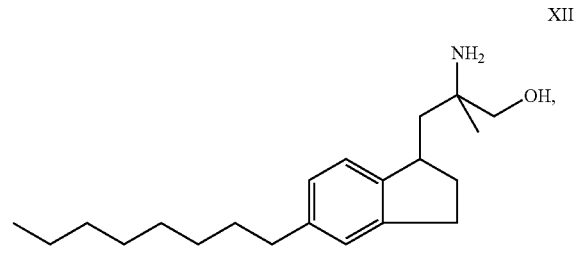
XIIA
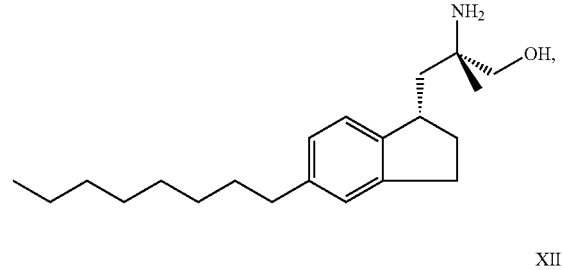
XIIB
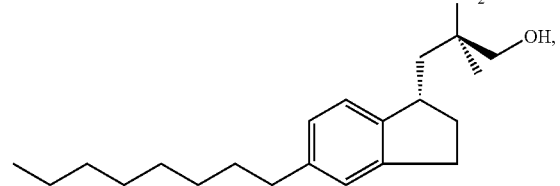
XIIC
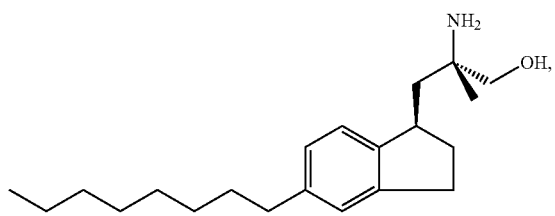
XIID
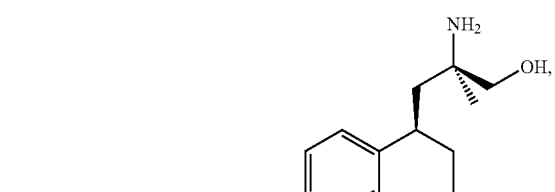
XIII
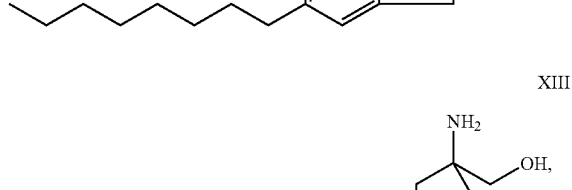
XIIIA
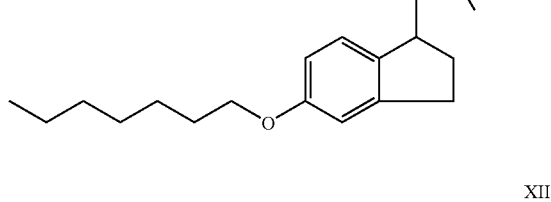
XIIIB
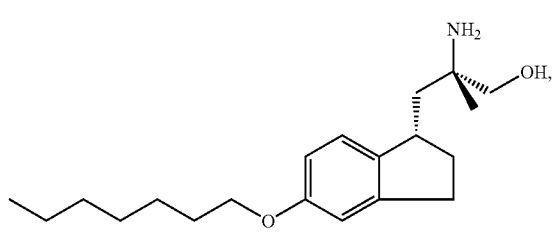
XIIIC
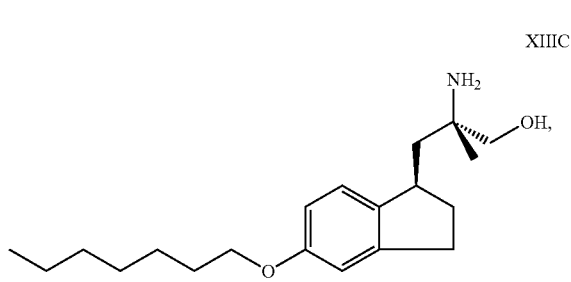

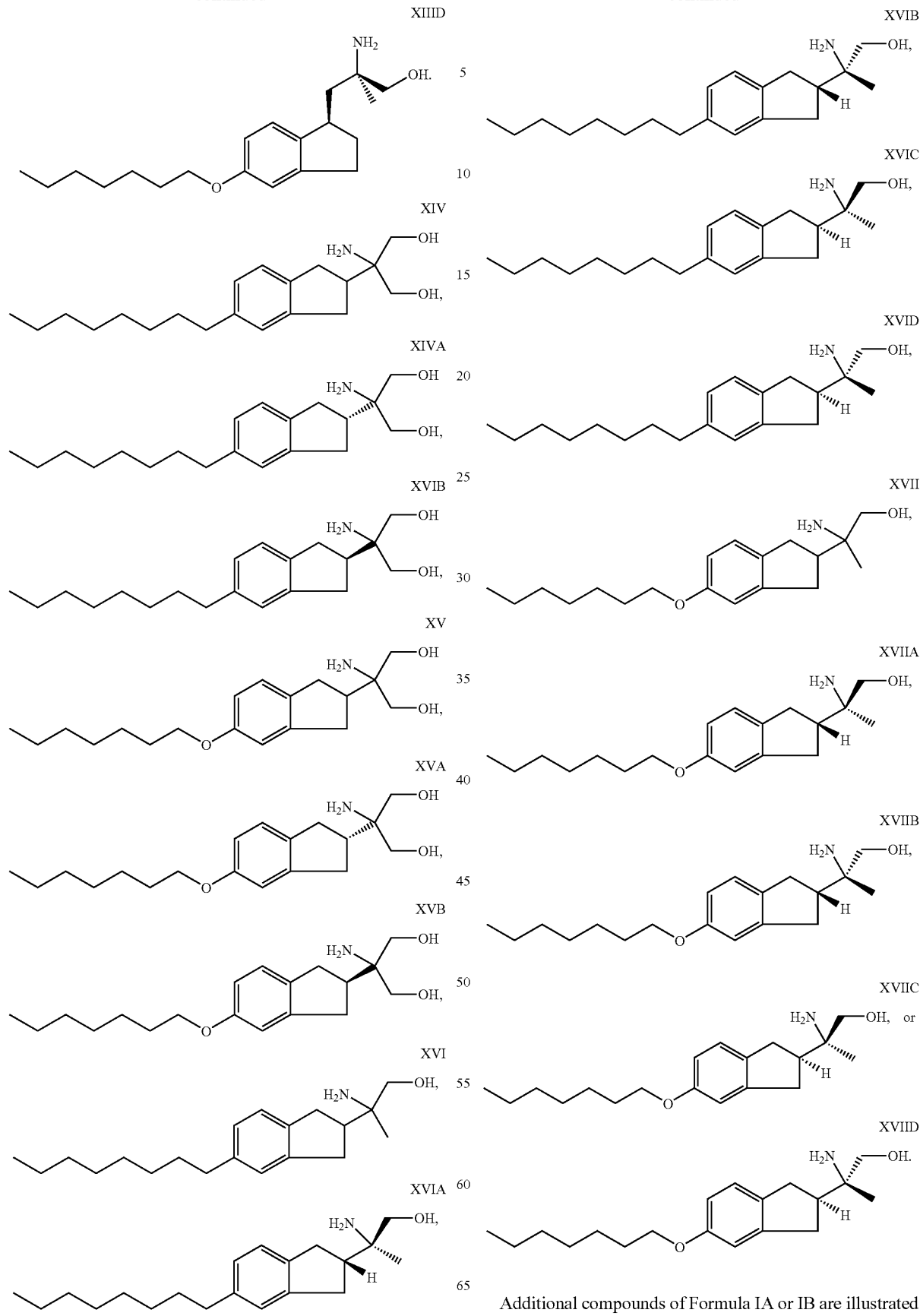
Additional compounds of Formula IA or IB are illustrated in table 1, below.

TABLE 1
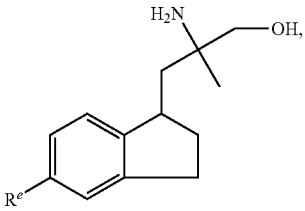
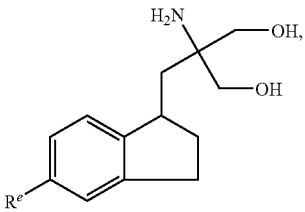
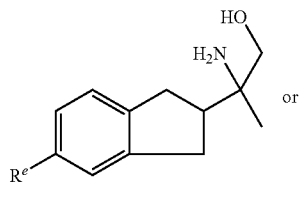 or
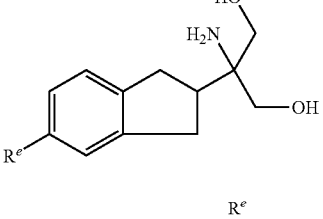
| Compound | R$^e$ |
|---|---|
| XX | 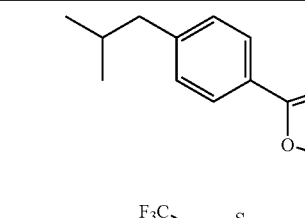 |
| XXI | 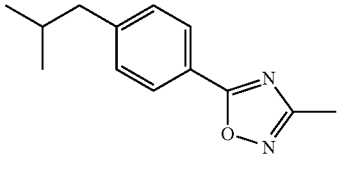 |
| XXII | 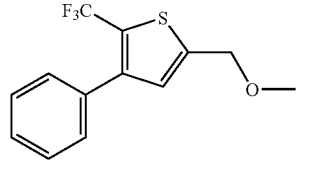 |
| XXIII | 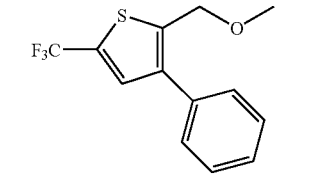 |
TABLE 1-continued
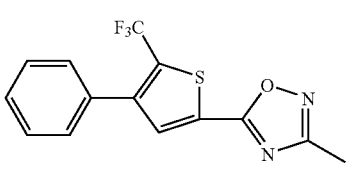
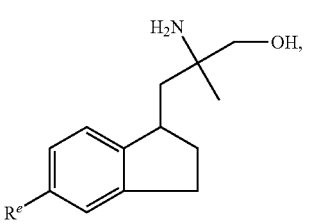
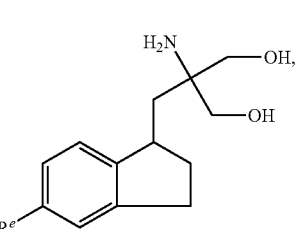 or
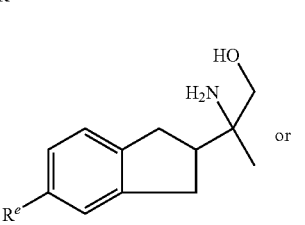
| Compound | R$^e$ |
|---|---|
| XXIV | 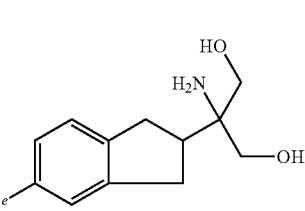 |
| XXV | 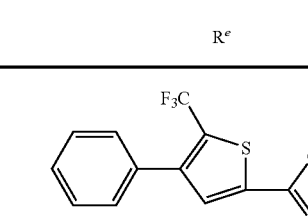 |
| XXXI | 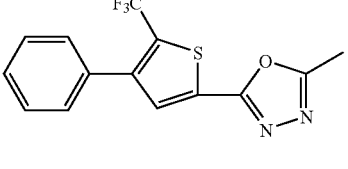 |
The compounds having formulas XX through XXV or XXXI also include all enantiomers thereof such as:

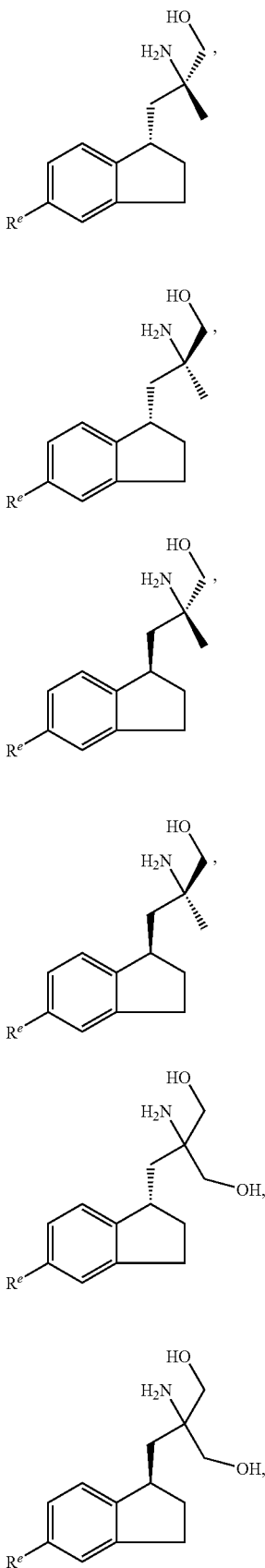
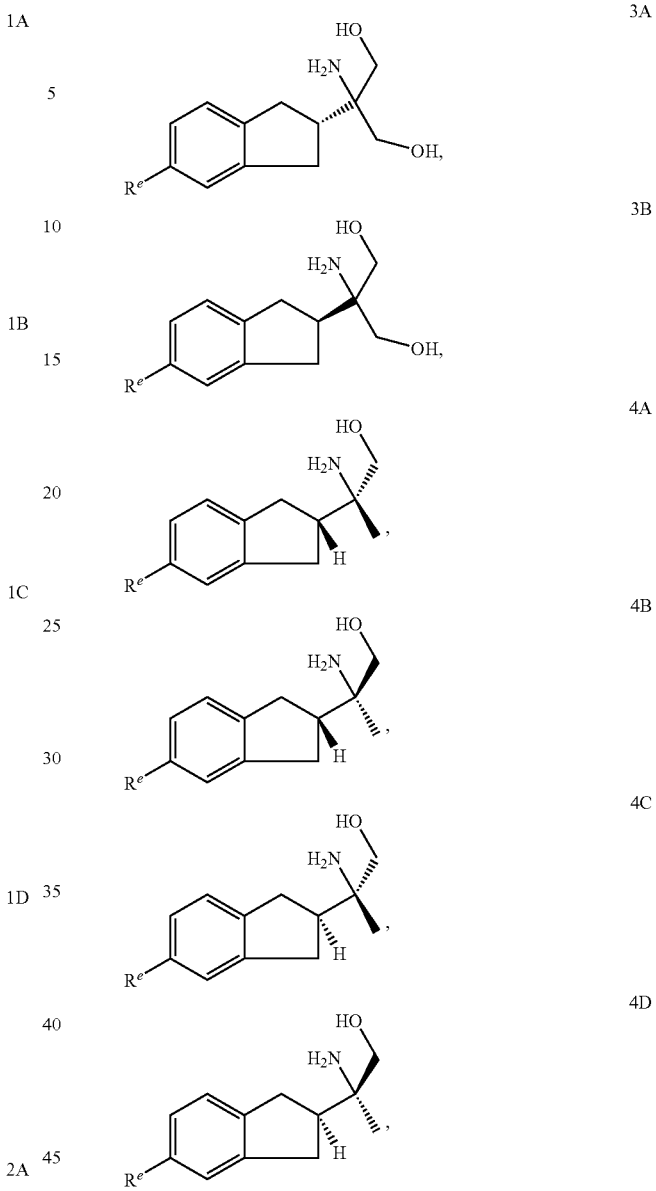

wherein the compounds include each of the $R^e$ groups from Table 1.

In another aspect, S1P receptor pro-drug compounds having the general structure of Formula IA, or IB, are provided by compounds with a mono-substituted ring system having the structure (VIIIA or VIIIB). In some embodiments of Formula I, the compound (e.g., X, or XI) may have only a single chiral center and that the amino carbon is pro-chiral, i.e., will become chiral following enzyme-catalyzed phosphorylation.

Without wishing to be bound by any particular theory, it is expected that the compounds described herein are pro-drugs, e.g., are activated by phosphorylation of the primary alcohol to form the mono-phosphorylated analog. Additionally, the active drugs are expected to be agonists at the S1P type 1 receptor.

In cases where compounds of Formula IA or IB are sufficiently basic or acidic to form stable nontoxic acid or base salts, preparation and administration of the compounds as pharmaceutically acceptable salts may be appropriate.

Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl) amines, alkenyl amines, dialkenyl amines, trialkenyl amines, substituted alkenyl amines, di(substituted alkenyl) amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl)amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of Formula IA or IB can be formulated as pharmaceutical compositions and administered to a mammalian host, such as a human patient in a variety of forms adapted to the chosen route of administration, e.g. orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g. when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula IA or IB to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula IA or IB can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula IA or IB in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit comprising an inhibitor compound of Formula IA or IB and instructional material that describes administering the inhibitor compound or a composition comprising the inhibitor compound to a cell or a subject. This should be construed to include other embodiments of kits that are known to those skilled in the art, such as a kit comprising a (preferably sterile) solvent for dissolving or suspending the inhibitor compound or composition prior to administering the compound or composition to a cell or a subject. Preferably, the subject is a human.

The disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the disclosed compounds.

Processes for preparing compounds of Formula IA or IB or for preparing intermediates useful for preparing compounds of Formula IA or IB are provided as further embodiments. Intermediates useful for preparing compounds of Formula IA or IB are also provided as further embodiments. The processes are provided as further embodiments and are illustrated in the schemes herein wherein the meanings of the generic radicals are as given above unless otherwise qualified.

Processes for preparing compounds of Formula IA or IB or for preparing intermediates useful for preparing compounds of Formula IA or IB are provided as further embodiments of the invention. Intermediates useful for preparing compounds of Formula IA or IB are also provided as further embodiments of the invention. The compounds of the invention can be prepared using starting materials and methods known in the art.

Figure 3:
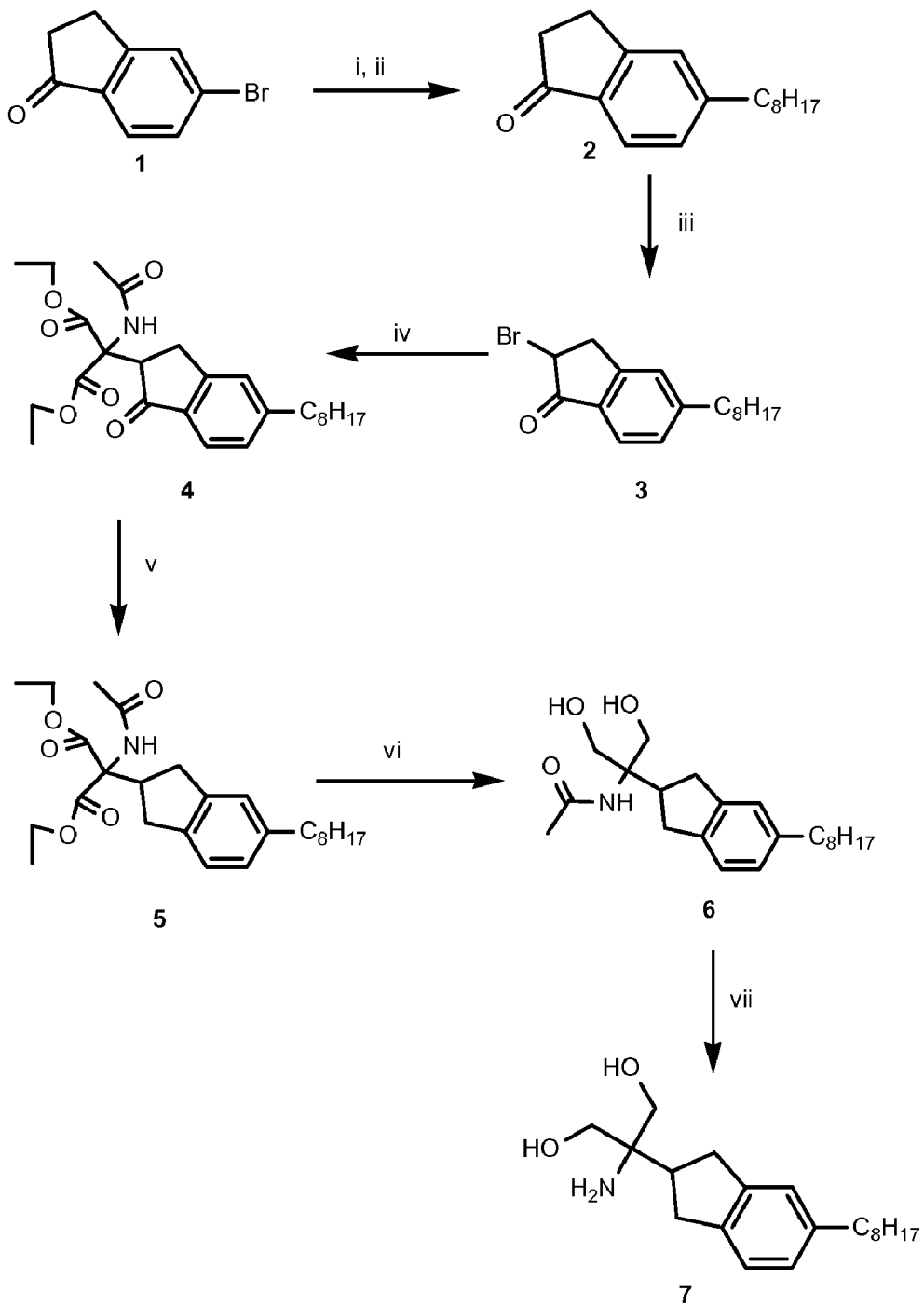
FIGS. 3-8 illustrate syntheses of compounds of Formula IA or IB.
Figure 4:
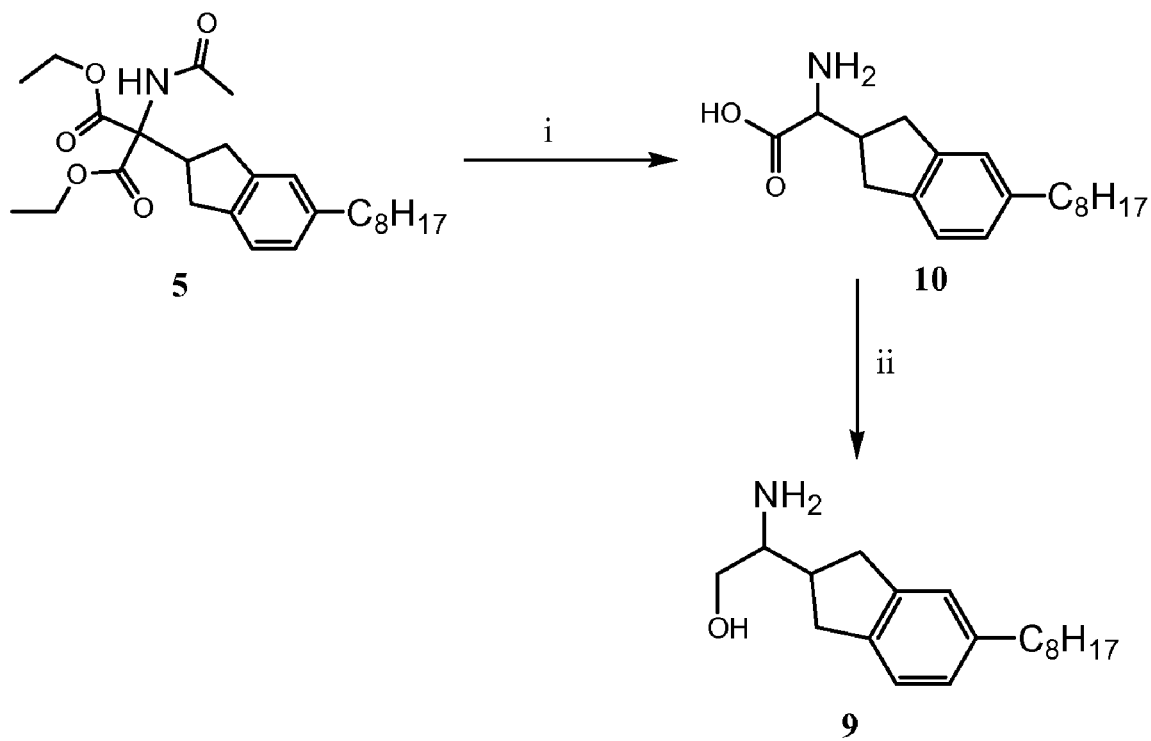
Figure 5:
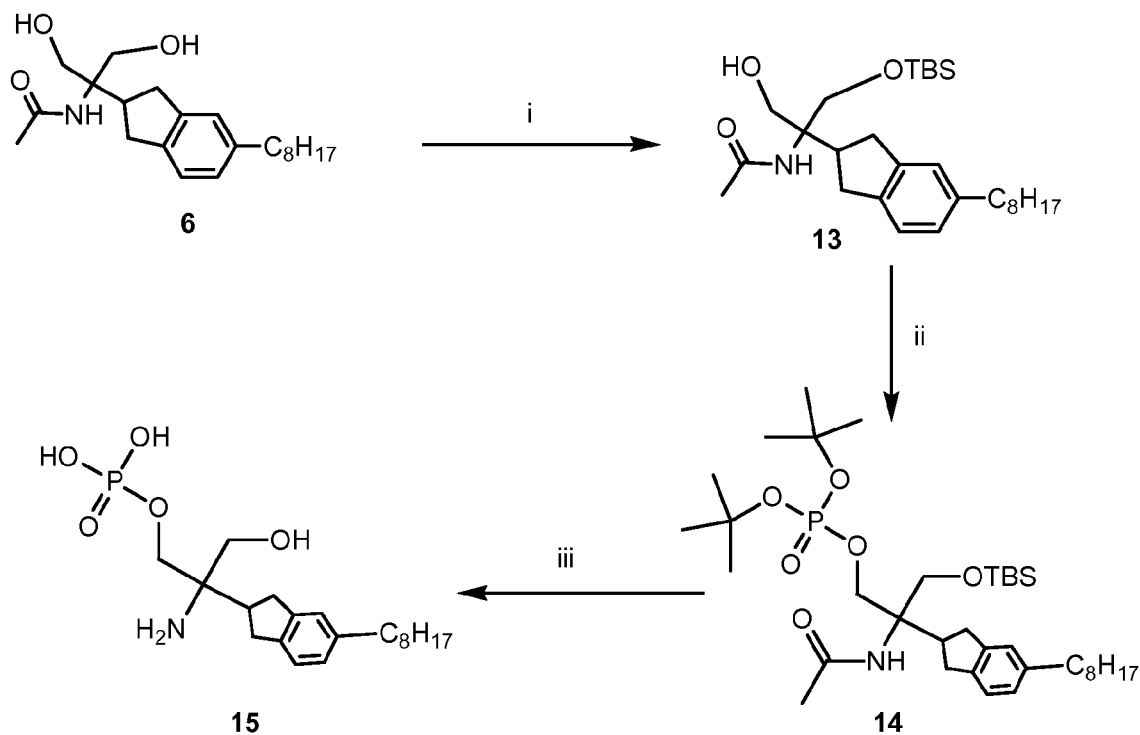
Figure 6:
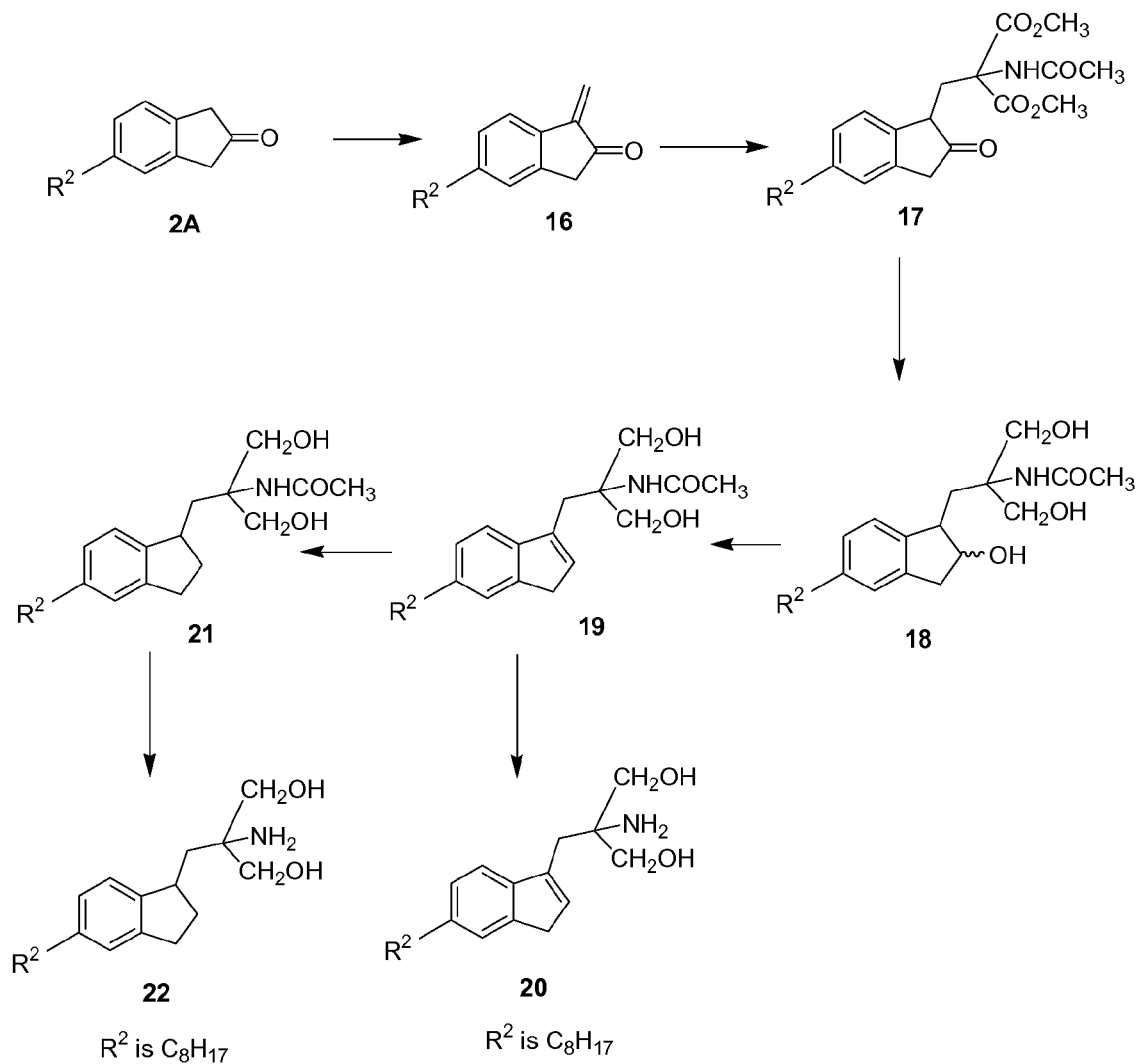

For example, the synthesis of target molecule, XIV is illustrated in Scheme 1 (FIG. 3) starting with 5-bromo-1-indanone (1). The synthetic route chosen (Scheme 1) begins with a Suzuki reaction attaching the 8 carbon chain (2). The product is brominated alpha to the ketone (3). Both of these reactions went smoothly and in good yield. The following reaction however, is an alkylation to add the 2-amino-1,3-propanediol in the form of diethyl acetamidomalonate. Sodium hydride is used as the base and provided the ketone diester (4) in 65-75% yield. The ketone is removed to provide methylene diester (5), followed by the ester reductions to provide the diol (6). Finally, the amide group is deprotected under basic conditions to form the resulting amine (7). The preparation of additional compounds are included in Scheme 2, Scheme 3, Scheme 4, Scheme 5, and Scheme 6 (See FIGS. 4-8).

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

EXAMPLES

Example 1

5-Octyl-indan-1-one (2). A Boron complex was first created by adding 1-octene (0.744 g, 6.633 mmol) to a stirring solution of 0.5M 9-BBN in THF (13.27 mL, 6.633 mmol). The reaction was left to stir at room temperature overnight. 3M NaOH (2.34 mL) was then added to the stirring solution followed by the addition of 5-Bromo-indan-1-one (1 g, 4.7 mmol) and Pd(Ph$_3$)$_4$ (0.145 g, 0.126 mmol). The reaction was refluxed for twelve hours. The resulting solution was concentrated and purified using silica gel chromatography eluding with hexanes-EtOAc (9:1). The reaction provided 2 (1.094 g, 4.48 mmol, 95%) as a clear liquid.

Example 2

2-Bromo-5-octyl-indan-1-one (3). To a solution of 2 (1.094 g, 4.48 mmol) in CHCl$_3$ (10 mL) at 40° C. was added Br$_2$ (0.23 mL, 4.477 mmol) dropwise over 15 minutes. The reaction was left to stir for 30 minutes. The resulting solution was concentrated and purified with silica gel chromatography eluding with hexanes-EtOAc (9:1). The reaction provided 3 (1.212 g, 3.75 mmol, 84%) as an orange liquid.

Example 3

2-Acetylamino-2-(5-octyl-1-oxo-indan-2-yl)-malonic acid diethyl ester (4). To a stirring solution of 60% NaH (1.194 g, 29.85 mmol) in DMF (5 mL) was added diethyl acetamidomalonate (6.484 g, 29.85 mmol) via cannula at 0° C. The solution was allowed to stir for 3 hours for anion to form. A solution of 3 (3.22 g, 9.95 mmol) in DMF (10 mL) was then added to then transferred to anion solution at 0° C. and left to stir over night at room temp. The reaction mixture was then poured over ice and extracted with EtOAc. The organic layer was washed with brine, dried with NaSO$_4$ and concentrated. The product was then purified with silica gel chromatography eluding with 70% hexanes-30% EtOAc. The reaction provided 4 (2.842 g, 6.184 mmol, 65%).

Example 4

2-Acetylamino-2-(5-octyl-indan-2-yl)-malonic acid diethyl ester (5). To a solution of Et$_3$SiH (1.014 g, 8.704 mmol) in CH$_2$Cl$_2$ (8 mL) was added 4 (0.213 g, 0.465 mmol) in CH$_2$Cl$_2$ (1.5 mL) dropwise at room temp under N$_2$. TiCl$_4$ (0.354 g, 1.858 mmol) was then added and the reaction left to stir at room temp over night. The reaction was then poured slowly over ice and extracted with CH$_2$Cl$_2$, the organic layer was then dried and concentrated. The product was then purified with silica gel chromatography eluding with 70% hexanes-30% EtOAc. The reaction provided 5 (0.149 g, 0.336 mmol, 72%).

Example 5

N-[2-Hydroxy-1-hydroxymethyl-1-(5-octyl-indan-2-yl)-ethyl]-acetamide (6). To a solution of LiBH$_4$ (0.564 mL, 1.127 mmol) at 0° C. was added 5 (0.1 g, 0.225 mmol). The mixture was allowed to stir at room temperature for 2 days. The reaction was quenched with water and extracted with EtOAc. The product was purified with silica gel chromatography eluding with 5% MeOH and 95% CH$_2$Cl$_2$. The reaction provided 6 (8 mg, 0.0029 mmol, 2%) and also 8 (5 mg, 0.0017 mmol, 0.74%).

Example 6

2-Amino-2-(5-octyl-indan-2-yl)-propane-1,3-diol (7). To a solution of 6 (8 mg, 0.022 mmol) in MeOH (0.1 mL) was added LiOH (0.01 g, 0.154 mmol). The reaction was refluxed for 2 hours. The resulting solution was concentrated and purified with silica gel chromatography eluding with 75% MeOH and 25% CH$_2$Cl$_2$. The reaction provided 7 (2.6 mg, 0.00822 mmol, 37%).

Example 7

Amino-(5-octyl-indan-2-yl)-acetic acid (10). To 10 mL of 12 M hydrochloric acid was added 5 (0.2 g, 0.451 mmol). Methanol was added until mix became homogenous and solution was allowed to reflux for 2 hours. The resulting mix was concentrated and co-evaporated with methanol and ether (3×10 mL). The reaction provided 10 (63 mg, 0.2076 mmol, 46%).

Example 8

2-Amino-2-(5-octyl-indan-2-yl)-ethanol (9). The carboxylic acid 10 is reduced with lithium aluminum hydride to provide compound (9).

Example 9

N-[1-(tert-Butyl-dimethyl-silanyloxymethyl)-2-hydroxy-1-(5-octyl-indan-2-yl)-ethyl]-acetamide (13). To a solution of 6 (0.166 g, 0.459 mmol) in CH$_2$Cl$_2$ (4 mL) at 0° C. was added tert-butyldimethylsilyl chloride (0.076 g, 0.5049 mmol) and triethyl amine (0.077 mL, 0.5508 mmol) drop wise. Mixture was allowed to warm to room temperature and stirred for 12 hours. The resulting product was washed with water and NH$_4$Cl, dried over Na$_2$SO$_4$ and concentrated. The product was purified with silica gel chromatography eluding with 70% hexanes and 30% EtOAc. The reaction provided 13 (87 mg, 0.183 mmol, 40%).

Example 10

Phosphoric acid 2-acetylamino-3-(tert-butyl-dimethyl-silanyloxy)-2-(5-octyl-indan-2-yl)-propyl ester di-tert-butyl ester (14). To 13 (0.087 g, 0.183 mmol) was added 0.45M solution of tetrazole in acetonitrile (0.82 mL, 0.366 mmol). A small amount of CH$_2$Cl$_2$ was also added to create a homogenous solution. This mixture was allowed to stir at room temperature for 1 hour. N,N-di-iso-propyl-di-tert-butyl-phosphoramidite (0.12 mL, 0.366 mmol) was then added and reaction left overnight. A solution of 30% H$_2$O$_2$ (0.1 mL, 0.732 mmol) was added to the reaction mixture and left to stir for an additional 2 hours. The product was purified with silica gel chromatography yielding 14 (10 mg, 0.015 mmol, 10%).

Example 11

Phosphoric acid mono-[2-amino-3-hydroxy-2-(5-octyl-indan-2-yl)-propyl]ester (15). To 1-1 solution of trifluoro acetic acid and CH$_2$Cl$_2$ was added 14 (10 mg, 0.015 mmol). The reaction was left to stir for 3 hours. When reaction complete, product was concentrated and repeatedly co-evaporated with diethyl ether (5×10 mL) to remove TFA. The product could not be purified by column chromatography. Diethyl ether was added to bring the product into solution, followed by the addition of hexanes to precipitate out product 15. The precipitate was then washed with water to remove ionic impurities and then concentrated.

Example 12

5-Octyl-1-methylene-indan-2-one (16). 5-Octyl-2-indanone, 2A (5.00 g, 20.5 mmol) and ethyl formate (3.70 g, 50 mmol) are dissolved in toluene (40 mL). Sodium hydride (1.15 g, 50 mmol) is added and the reaction brought to reflux for 6 hours with continuous removal of water. The reaction mixture is cooled to room temperature and p-toluenesulfonyl chloride (3.75 g, 21.0 mmol) dissolved in THF (20 mL) added. The reaction mixture is maintained under inert atmosphere for 12 hours and filtered. The solvent is removed in vacuo to yield a viscous liquid residue. The crude reaction mixture is used without purification in the next step.

Example 13

Figure 7:
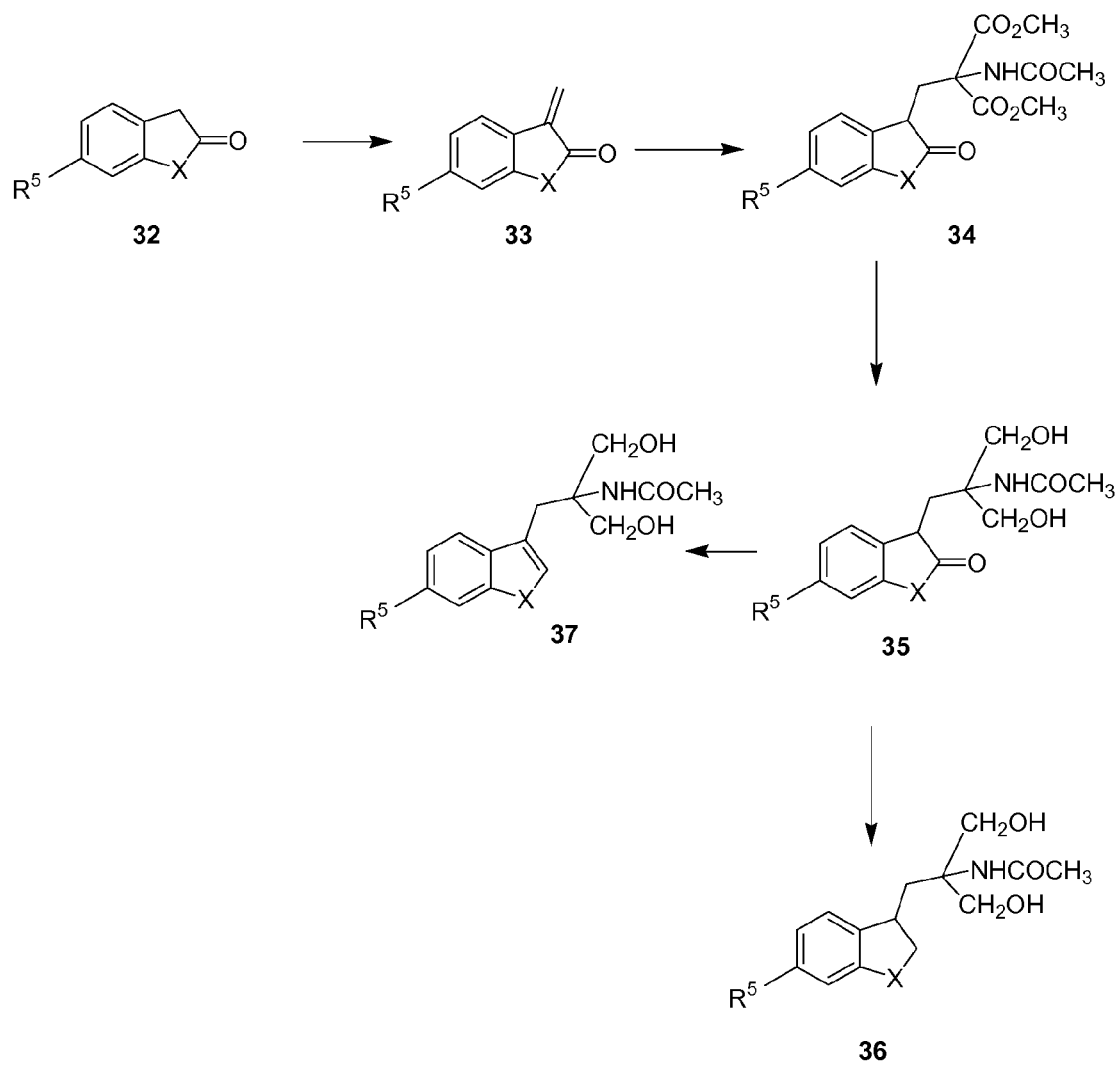
Figure 8:
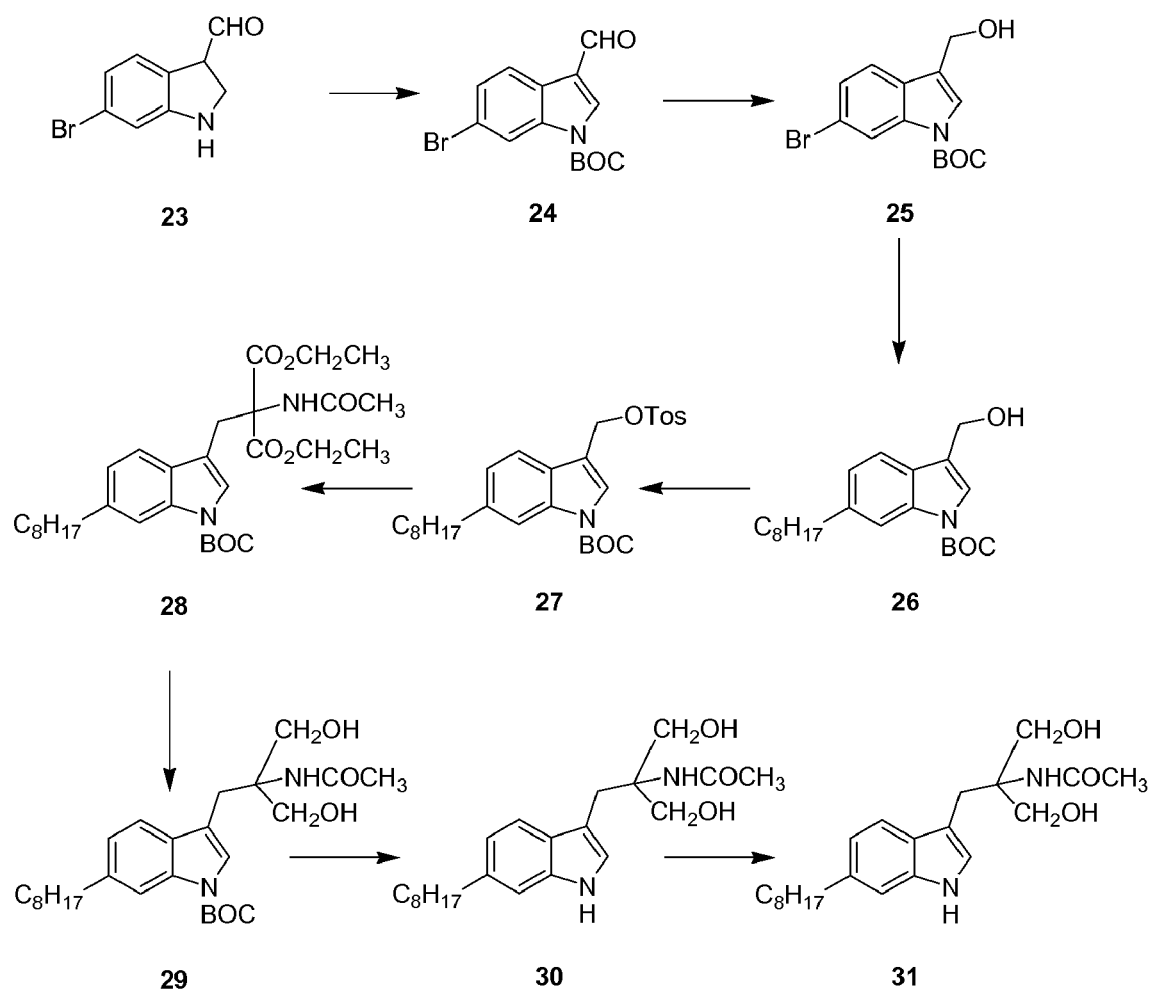

2-Acetylamino-2-(5-octyl-2-oxo-indan-1-ylmethyl)-malonic acid dimethyl ester (17). Diethyl acetamidomalonate (4.55 g, 21.0 mmol) is dissolved in THF (40 mL). Sodium hydride (0.600 g, 25.0 mmol) is added. The reaction is brought to reflux for 2.0 hours. The residue (compound 16) from Example 12, dissolved in THF (40 mL) is added. The reaction is maintained at reflux for an additional 4 hours, cooled, and poured into a separatory funnel containing ether (100 mL) and water (75 mL). The ether layer is separated and the aqueous layer is re-extracted with ether (100 mL). The combined organic layers are dried over MgSO$_4$ and the solvent removed in vacuo. The residue is chromatographed over silica gel yielding 17 (FIG. 7).

Example 14

N-[1,1-Bis-hydroxymethyl-2-(2-hydroxy-5-octyl-indan-1-yl)-ethyl]-acetamide (18). To a solution of LiBH$_4$ (450 mg, 20.4 mmol) in THF (20 mL) at 0° C. is added 17 (1.35 g, ~3.1 mol). The reaction mixture is warmed to room temperature and stirred under inert atmosphere for 2 days. The reaction is quenched with water and extracted with EtOAc. The product is then purified over silica gel eluting with 8% methanol/92% methylene chloride to yield 18 (FIG. 7).

Example 15

N-[1,1-Bis-hydroxymethyl-2-(5-octyl-3H-inden-1-yl)-ethyl]-acetamide (19). Compound 18 (85 mg, 022 mmol) is dissolved in toluene (10 mL), toluenesulphonic acid (~5 mg) is added, and the reaction heated to reflux for 3 hours with continuous removal of water from the condensed azeotrope. The reaction is cooled, then poured into aqueous bicarbonate (5% w/w, 10 mL) and the aqueous layer extracted with ether (5 mL) twice. The organic layers are combined and removed in vacuo to provide the crude residue that upon silica gel chromatography provide 19.

Example 16

N-[1,1-Bis-hydroxymethyl-2-(5-octyl-indan-1-yl)-ethyl]-acetamide (20). Compound 19 (18 mg, 0.047 mmol) is dissolved in methanol (0.50 mL) and LiOH (0.04 g, 0.60 mmol) is added. The reaction is heated and maintained at reflux for 2 hours, diluted with ether (5 mL). The organic layer is washed with water (1×5 mL) and brine (1×5 mL). The combined organic layer is concentrated in vacuo then purified by silica gel chromatography eluding with 75% methanol and 25% methylene chloride.

Example 17

6-Bromo-3-formyl-indole-1-carboxylic acid tert-butyl ester (24). 6-Bromoindole-3-carboxaldehyde, 23 (5.0 g, 22.3 mmol) is dissolved in methylene chloride (40 mL), then cooled to 0° C. and tert-butylchloroformate (3.40 g, 25.0 mmol) and triethyl amine (2.50 g, 25.0 mmol) are added over 5 minutes. The reaction is maintained at reflux, under inert atmosphere for 3 hours. The reaction is cooled, filtered and the solvent removed in vacuo. The residue composed primarily of compound 24 is used in the Example 18 without purification. (See, e.g., G. Wille and W. Steglich, *Synthesis*, 2001, 759-762 for a related procedure.)

Example 18

6-Bromo-3-hydroxymethyl-indole-1-carboxylic acid tert-butyl ester (25). The protected aldehyde residue, 24, from step 1 is dissolved in methanol (50 mL) at 0° C. Sodium borohydride (0.750 g, 22.0 mmol) is added to the solution, which is maintained at 0° C. After completion, the reaction is quenched with aqueous 0.5 N hydrochloric acid and poured into a separatory funnel containing methylene chloride (200 mL) and water (100 mL). The organic layer is removed and the aqueous layer extracted with methylene chloride (2×50 mL). The combined organic layers are dried over MgSO$_4$ and the solvent removed in vacuo. The residue is chromatographed on silica gel with ethyl acetate (75%)/hexanes (25%) to yield compound 25.

Example 19

3-Hydroxymethyl-6-octyl-indole-1-carboxylic acid tert-butyl ester (26). An octyl boronate intermediate is generated by adding 1-octene (1.38 g, 14.1 mmol) to a solution of 9-BBN in THF (28.3 mL of a 0.5 M solution, 14.1 mmol). The reaction mixture is stirred at room temperature overnight. An aqueous solution of sodium hydroxide (5.0 mL of a 3.0 M solution) is added, followed by the addition of compound 25 (3.10 g, 10.0 mmol) and Pd[P(Ph)$_3$]$_4$ (0.310 g, 0.270 mmol). The reaction is brought to reflux and maintained for 12 hours under an inert atmosphere. The reaction is cooled, filtered, concentrated in vacuo and the residue purified using silica gel chromatography with hexane/ethyl acetate (75:25) as solvent.

Example 20

2-Acetylamino-2-(1-tert-butoxycarbonyl-6-octyl-1H-indol-3-ylmethyl)-malonic acid dimethyl ester (28). Diethyl acetamidomalonate (6.50 g, 29.9 mmol) is added to a solution of sodium hydride (60% in oil, 1.20 g, 29.9 mmol) in anhydrous DMF (5.0 mL) at 0° C. The solution is allowed to stir for 3 hours at 0° C. for an anion to form.

In a separate vessel, compound 26 (3.00 g, 9.0 mmol) is added to a suspension of sodium hydride (60% in oil, 0.40 g, 10.0 mmol) in THF (5 mL) at 0° C. After 1 hour, para-toluenesulfonyl chloride (1.80 g, 9.0 mmol) is added and the reaction continued for an additional 2 hours at room temperature to form tosylate 27. The DMF solution of diethyl acetamidomalonate anion is added to the THF/tosylate solution via cannula and the resulting solution stirred overnight at room temperature. The reaction mixture is poured over ice and extracted with methylene chloride (2×25 mL). The combined organic layers are washed with brine, dried over MgSO$_4$ and concentrated in vacuo. The residue is purified using silica gel chromatography with hexanes (50%)-ethyl acetate (50%) to afford compound 28.

Example 21

3-(2-Acetylamino-3-hydroxy-2-hydroxymethyl-propyl)-6-octyl-indole-1-carboxylic acid tert-butyl ester (29). Compound 28 (2.50 g, 4.75 mmol) is added to a solution of LiBH$_4$ (0.525 g, 23.8 mmol) in THF (20 mL) at room temperature under inert atmosphere. The reaction is stirred for 2 days, then quenched with water (5.0 mL) and then extracted with methylene chloride (2 and 25 mL). The combined organic layers are dried over MgSO$_4$ and concentrated in vacuo. The residue is purified using silica gel chromatography with methanol (5%)-methylene chloride (95%) to give compound 29.

Example 22

N-[1,1-Bis-hydroxymethyl-2-(6-octyl-1H-indol-3-yl)-ethyl]-acetamide (30). Compound 29 (200 mg, 0.46 mmol) is added to methylene chloride (10 mL) and the solution is cooled to −40° C. Trifluoroacetic acid (3.0 mL) is added and the reaction is stirred for 1 hour maintaining the temperature. The reaction is quenched with methanol (10 mL) at −40° C. and then partitioned between methylene chloride (25 mL) and aqueous sodium hydroxide (1.0 N, 25 mL). The aqueous layer is back extracted with methylene chloride (2×10 mL) and the combined organic layers are washed with aqueous sodium hydroxide (1.0 N, 3×10 mL), then brine and dried over MgSO$_4$. The organic layer is evaporated to dryness and the residue purified using silica gel chromatography with methanol (10%)-methylene chloride (90%) to give compound 30.

Example 23

Compound 30 (72 mg, 0.020 mmol) is dissolved in methanol (3.0 mL) and LiOH (100 mg, 1.54 mmol) is added. The reaction is heated at reflux for 2 hours, then partitioned between methylene chloride (10 mL) and water (5 mL). The aqueous layer is extracted with methylene chloride (2×5 mL) and the combined organics are then dried over MgSO$_4$. The organic layer is evaporated to dryness. The residue purified using silica gel chromatography with methanol (25%)-methylene chloride (75%) to give compound 31.

The assays below are standard literature reported assays known in the art for confirming and quantifying the activity of the disclosed compounds.

Example 24

Sphingosine Kinase Assay

Recombinant sphingosine kinase type 2 (SPHK2) is prepared by forcing the expression of the mouse or human recombinant enzyme by transfecting the relevant plasmid DNA into HEK293T or CHO K1 cells. After about 60 hours, cells are harvested, broken and the non-microsomal (e.g., soluble) fraction is retained. The broken cell supernatant fluid containing the recombinant enzyme is mixed with test compounds (FTY720, AA151, VIII and XVIII) (5-50 micromolar) and γ-32P-ATP and incubated for 0.5-2.0 hours at 37° C. The lipids in the reaction mixture are extracted into an organic solvent and displayed by normal phase thin layer chromatography. The radio-labeled bands are detected by autoradiography, scraped from the plate and quantified by scintillation counting. The test compounds are used at a concentration of about 50 μM, incubation time is about 20 minutes.

Example 25

GTPγS-35 Binding Assay

This assay illustrates agonist activation of G protein coupled receptors (GPCRs) in isolation. The assay forces expression concomitantly of a recombinant GPCR (e.g., the S1P1-5 receptor) and each of the three subunits (e.g., α-i2, β-1, and γ-2) of a heterotrimeric G protein in a HEK293T cell by transfecting the cell with four plasmid DNAs encoding the respective proteins. About 60 hours after transfection the cells are harvested, broken, the nucleus discarded, and the crude microsomes are prepared from the remainder. Agonist (e.g., S1P) stimulation of the receptor-G protein complex on the microsomes results in the exchange of GTP for GDP on the α-subunit in a dose-dependent manner. The GTP-bound α-subunit is detected using a GTP analog (GTPγS-35), which is a radionuclide (sulfur-35) labeled phosphothionate that is not hydrolyzed to GDP. The microsomes with the adherent G proteins are collected by filtration and the bound GTPγS-35 quantified in a liquid scintillation counter. The assay yields relative potency (EC$_{50}$ values) and maximum effect (efficacy, E$_{max}$). Antagonist activity is detected as rightward shifts in the agonist dose-response curve in the presence of a fixed amount of antagonist. If the antagonist behaves competitively, the affinity of the receptor/antagonist pair (K$_i$) can be determined. The assay is described in Davis, M. D., J. J. Clemens, T. L. Macdonald and K. R. Lynch (2005) "S1P Analogs as Receptor Antagonists" Journal of Biological Chemistry, vol. 280, pp. 9833-9841.

Example 26

Lymphopenia Assay

The test compounds (e.g., primary alcohols) are dissolved in 2% hydroxypropyl beta-cyclodextrin and introduced into groups of mice by oral gavage at doses from 0.01, 1.0 and 10 mg/kg body weight. At intervals, e.g., 24 hours, 48 hours, or 96 hours the mice are lightly anesthetized and ca. 0.1 mL of blood is drawn from the orbital sinus. The number of lymphocytes (in thousands per microliter of blood; normal is 4-11) is determined using a Hemavet blood analyzer.

Example 27

Heart Rate Assay

Mice are dosed with test compounds (intravenous, 3 mg/kg) or vehicle (2% hydroxypropyl beta-cyclodextrin) and the heart rate measured at 1 hour post dosing. Heart rate is captured in unrestrained, conscious animals using the ECG-enie™ system.

The invention should not be construed to be limited solely to the assays and methods described above, but should be construed to include other methods and assays as well. Other methods that are used but not described above are well known and within the competence of one of ordinary skill in the art of chemistry, biochemistry, molecular biology, and clinical medicine. One of ordinary skill in the art will know that other assays and methods are available to perform the procedures described above.

The abbreviations used above have their conventional meaning within the clinical, chemical, and biological arts. In the case of any inconsistencies, the present disclosure, including any definitions therein will prevail.

The invention claimed is:

1. A compound of Formula IA or IB:

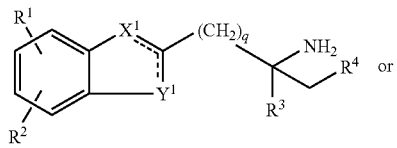
IA

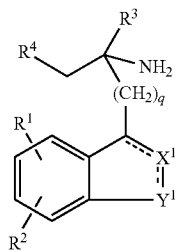
IB wherein $X^1$ and $Y^1$ are independently, $CR^a$ or $CR^aR^b$;

$R^1$ and $R^2$ are independently hydrogen, halo, halo($C_1$-$C_{10}$) alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl;

wherein the alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $R^1$ or $R^2$ alkyl groups can be independently replaced with non-peroxide oxygen, sulfur or $NR^c$; and the alkyl groups of $R^3$ are optionally substituted with 1, or 2 hydroxy groups; or $R^2$ can be a group having formula II, III, IV, V, or VI;

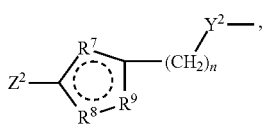
II

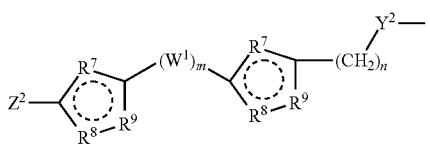
III

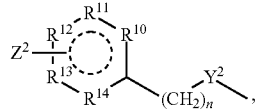
IV

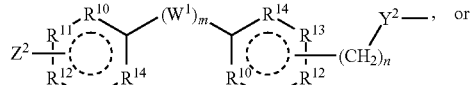
V

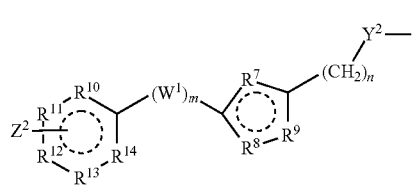
VI wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{18}$;

each $R^{15}$, $R^{16}$ and $R^{17}$ is independently hydrogen, halo, ($C_1$-$C_{10}$)alkyl, ($C_6$-$C_{10}$)aryl, ($C_1$-$C_{10}$)alkyl substituted with halo, hydroxy, ($C_1$-$C_{10}$)alkoxy, or cyano; and where $R^{18}$ can be hydrogen or ($C_1$-$C_{10}$)alkyl;

where $Z^2$ is hydrogen, halo, halo($C_1$-$C_{10}$)alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl; wherein the alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $Z^2$ alkyl groups can be independently replaced with non-peroxide oxygen, sulfur or $NR^c$;

--- indicates one or more optional double bonds;

wherein $Y^2$ is a bond, O, S, C=O, or $NR^c$, $CH_2$; $W^1$ is a bond, —$CH_2$— and m is 1, 2, or 3, or $W^1$ is (C=O)($CH_2$)$_{1-5}$ and m is 1; wherein $W^1$ is optionally interrupted with non-peroxide O, S, C=O, or $NR^c$;

n is 0, 1, 2, or 3; --- represents an optional double bond;

q is 1, 2, or 3;

$R^3$ is hydrogen, ($C_1$-$C_{10}$)alkyl, hydroxy($C_1$-$C_{10}$)alkyl or ($C_1$-$C_{10}$)alkoxy; and $R^4$ is hydroxyl (—OH), phosphate (—$OPO_3H_2$), phosphonate (—$CH_2PO_3H_2$), or alpha-substituted phosphonate;

each $R^a$, $R^b$, $R^c$, and $R^d$ is independently hydrogen, $CF_3$ or ($C_1$-$C_{10}$)alkyl; or a pharmaceutically acceptable salt or ester thereof.

2. The compound of claim 1, wherein $R^1$ is hydrogen, fluorine, chlorine, bromine, trifluoro-methyl, methoxy, ($C_1$-$C_6$)alkyl, ($C_1$-$C_6$)haloalkyl, ($C_1$-$C_6$)alkyl substituted with, alkoxy or cyano, alkyl-substituted aryl, aryl-substituted alkyl, or aryl-substituted arylalkyl.

3. The compound of claim 2, wherein $R^1$ is hydrogen, trifluoro-methyl, or —$CH_2CF_3$.

4. The compound of claim 2, wherein $R^1$ is benzyl, phenylethyl, or benzyl substituted with methyl.

5. The compound of claim 1, wherein $R^2$ is

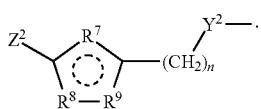

6. The compound of claim 1, wherein $R^2$ is:

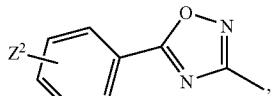

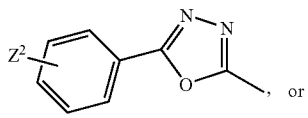

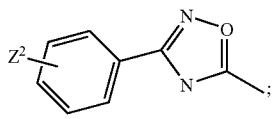

wherein $Z^2$ is $(CH_3)_3C-$, $CH_3CH_2(CH_3)_2C-$, $CH_3CH_2CH_2-$, $CH_3(CH_2)_2CH_2-$, $CH_3(CH_2)_4CH_2-$, $(CH_3)_2CHCH_2-$, $(CH_3)_3CCH_2-$, $CH_3CH_2O-$, $(CH_3)_2CHO-$, or $CF_3CH_2CH_2-$ or a group having the formula:

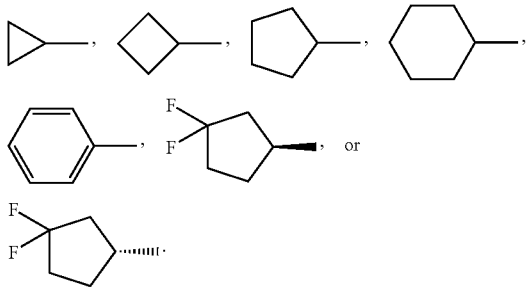

7. The compound of claim 6, wherein $R^2$ is:

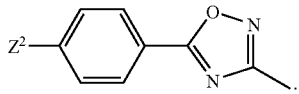

8. The compound of claim 6, wherein $R^2$ is:

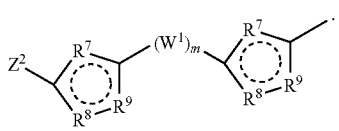

9. The compound of claim 8, wherein $R^2$ is

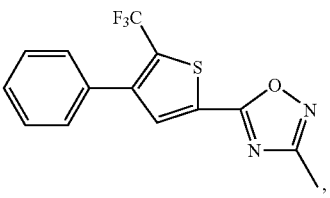

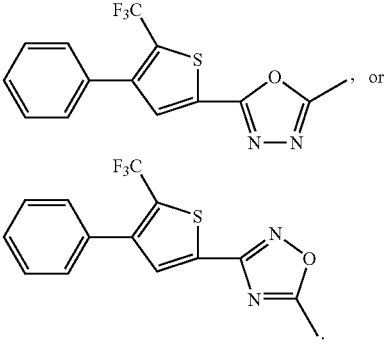

10. The compound of claim 1, wherein $R^2$ is methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

11. The compound of claim 1, wherein $X^1$ and $Y^1$ are both $CH_2$.

12. The compound of claim 1, wherein $R^3$ is hydrogen, methyl, hydroxymethyl, ethyl, or hydroxyethyl.

13. The compound of claim 1, having the formula

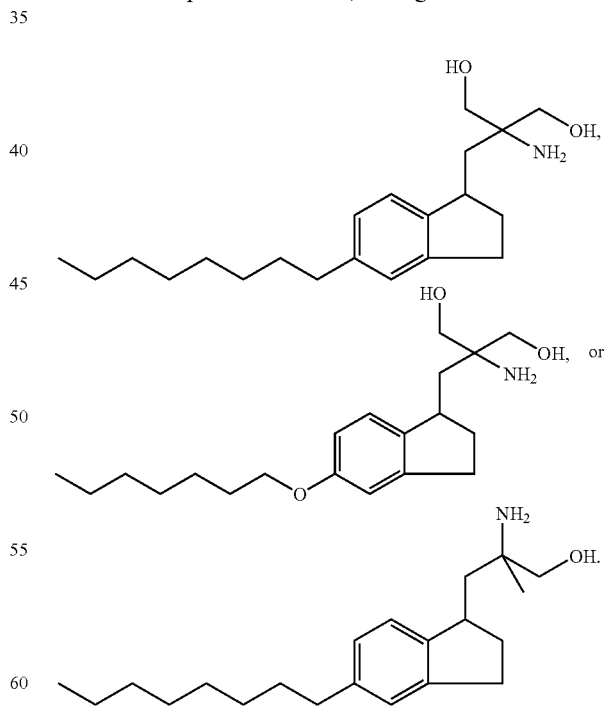

14. A method for treatment of a pathological condition or symptom in a mammal, wherein the activity of sphingosine 1-phosphate receptors is implicated and agonism of such activity is desired, comprising administering to said mammal an effective amount of a compound of claim 1 wherein the pathological condition or symptom is uveitis, type I diabetes, rheumatoid arthritis, inflammatory bowel diseases, multiple sclerosis, or altering of lymphocyte trafficking.

15. The method of claim 14, wherein the pathological condition or symptom is uveitis, type I diabetes, rheumatoid arthritis, inflammatory bowel diseases, or multiple sclerosis.

16. The method of claim 15, wherein the pathological condition or symptom is multiple sclerosis.

17. The method of claim 14, wherein the pathological condition or symptom is altering of lymphocyte trafficking.

18. The method of claim 17, wherein altering lymphocyte .trafficking provides prolonged allograft survival.

19. A method for treatment of a pathological condition or symptom in a mammal, wherein the activity S1P lyase is implicated and inhibition of the S1P lyase is desired, comprising administering to said mammal an effective amount of a compound of claim 1 wherein the pathological condition or symptom is uveitis, type I diabetes, rheumatoid arthritis, inflammatory bowel diseases, multiple sclerosis, or altering of lymphocyte trafficking.

* * * * *